(12) United States Patent
Kriesel

(10) Patent No.: US 8,133,204 B1
(45) Date of Patent: Mar. 13, 2012

(54) MEDICAMENT DISPENSER

(75) Inventor: Marshall S. Kriesel, St. Paul, MN (US)

(73) Assignee: BioQuiddity, Inc., San Francisco, CA (US)

( * ) Notice: Subject to any disclaimer, the term of this patent is extended or adjusted under 35 U.S.C. 154(b) by 0 days.

(21) Appl. No.: 12/925,072

(22) Filed: Oct. 12, 2010

(51) Int. Cl.
*A61M 5/00* (2006.01)

(52) U.S. Cl. ........................................ 604/132

(58) Field of Classification Search .......... 604/131, 604/132, 134
See application file for complete search history.

(56) References Cited

U.S. PATENT DOCUMENTS

| | | | | |
|---|---|---|---|---|
| 7,828,770 | B2 * | 11/2010 | Bivin et al. | 604/132 |
| 2007/0156090 | A1 * | 7/2007 | Kriesel | 604/131 |
| 2007/0219501 | A1 * | 9/2007 | Kriesel et al. | 604/185 |
| 2007/0219502 | A1 * | 9/2007 | Kriesel et al. | 604/185 |
| 2008/0027376 | A1 * | 1/2008 | Kriesel et al. | 604/84 |
| 2008/0027386 | A1 * | 1/2008 | Kriesel et al. | 604/132 |
| 2008/0051701 | A1 * | 2/2008 | Kriesel | 604/82 |
| 2008/0228129 | A1 * | 9/2008 | Kriesel et al. | 604/19 |
| 2008/0243077 | A1 * | 10/2008 | Bivin et al. | 604/131 |
| 2008/0319385 | A1 * | 12/2008 | Kriesel et al. | 604/88 |
| 2009/0024083 | A1 * | 1/2009 | Kriesel et al. | 604/86 |
| 2009/0108511 | A1 * | 4/2009 | Bivin et al. | 267/167 |
| 2009/0112149 | A1 * | 4/2009 | Kriesel et al. | 604/19 |
| 2009/0112163 | A1 * | 4/2009 | Bivin et al. | 604/132 |
| 2009/0254067 | A1 * | 10/2009 | Kriesel | 604/890.1 |
| 2009/0275888 | A1 * | 11/2009 | Kriesel et al. | 604/86 |
| 2010/0056995 | A1 * | 3/2010 | Kriesel | 604/83 |
| 2010/0056996 | A1 * | 3/2010 | Kriesel | 604/85 |
| 2010/0056997 | A1 * | 3/2010 | Kriesel | 604/85 |
| 2010/0056998 | A1 * | 3/2010 | Kriesel et al. | 604/85 |
| 2010/0094203 | A1 * | 4/2010 | Kriesel et al. | 604/66 |
| 2010/0094218 | A1 * | 4/2010 | Kriesel et al. | 604/132 |
| 2010/0094219 | A1 * | 4/2010 | Kriesel et al. | 604/134 |
| 2010/0222741 | A1 * | 9/2010 | Bivin et al. | 604/132 |
| 2010/0241074 | A1 * | 9/2010 | Bivin et al. | 604/132 |
| 2010/0312175 | A1 * | 12/2010 | Kriesel et al. | 604/30 |
| 2010/0312187 | A1 * | 12/2010 | Kriesel et al. | 604/132 |
| 2011/0077593 | A1 * | 3/2011 | Kriesel et al. | 604/134 |
| 2011/0077594 | A1 * | 3/2011 | Kriesel et al. | 604/134 |
| 2011/0082422 | A1 * | 4/2011 | Joshi et al. | 604/113 |
| 2011/0092904 | A1 * | 4/2011 | Kriesel et al. | 604/131 |
| 2011/0098645 | A1 * | 4/2011 | Kriesel et al. | 604/132 |
| 2011/0251556 | A1 * | 10/2011 | Kriesel et al. | 604/132 |

* cited by examiner

*Primary Examiner* — Nicholas Lucchesi
*Assistant Examiner* — Aarti B Berdichevsky
(74) *Attorney, Agent, or Firm* — James E. Brunton

(57) ABSTRACT

A dispensing device for dispensing medicaments to a patient comprising a plurality of threadably interconnectable sub-assemblies. One of these sub-assemblies houses a novel collapsible fluid reservoir defining component that is carried by a carriage while another comprises a fluid delivery and control assembly that includes a novel flow control means that functions to control the flow of medicinal fluid from the fluid reservoir of the collapsible reservoir defining component toward the patient via a plurality of fluid flow control passageways. In one form of the invention the collapsible fluid reservoir is filled at time of manufacture. In another form of the invention the collapsible fluid reservoir can be filled in the field using a syringe assembly.

20 Claims, 27 Drawing Sheets

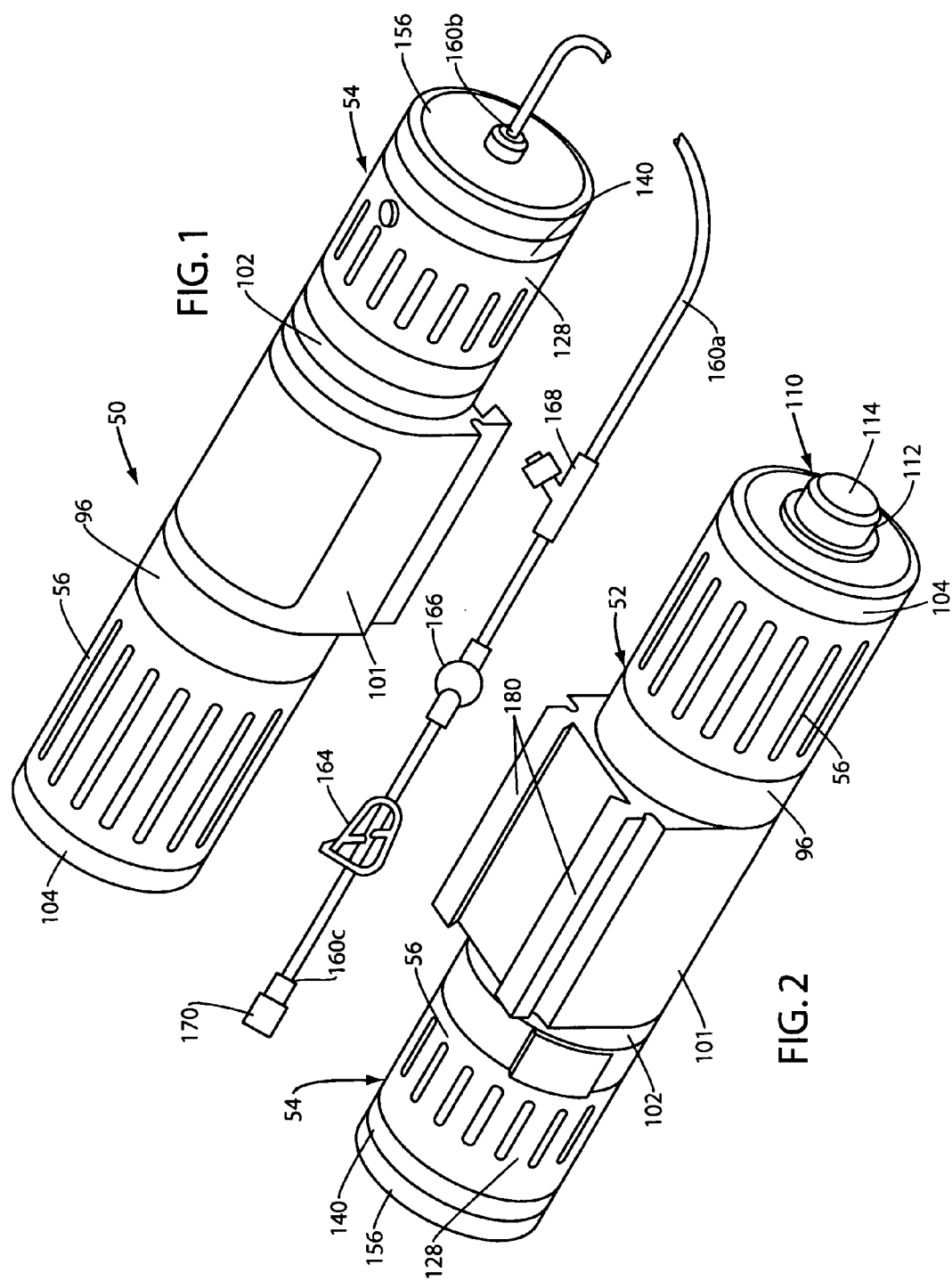

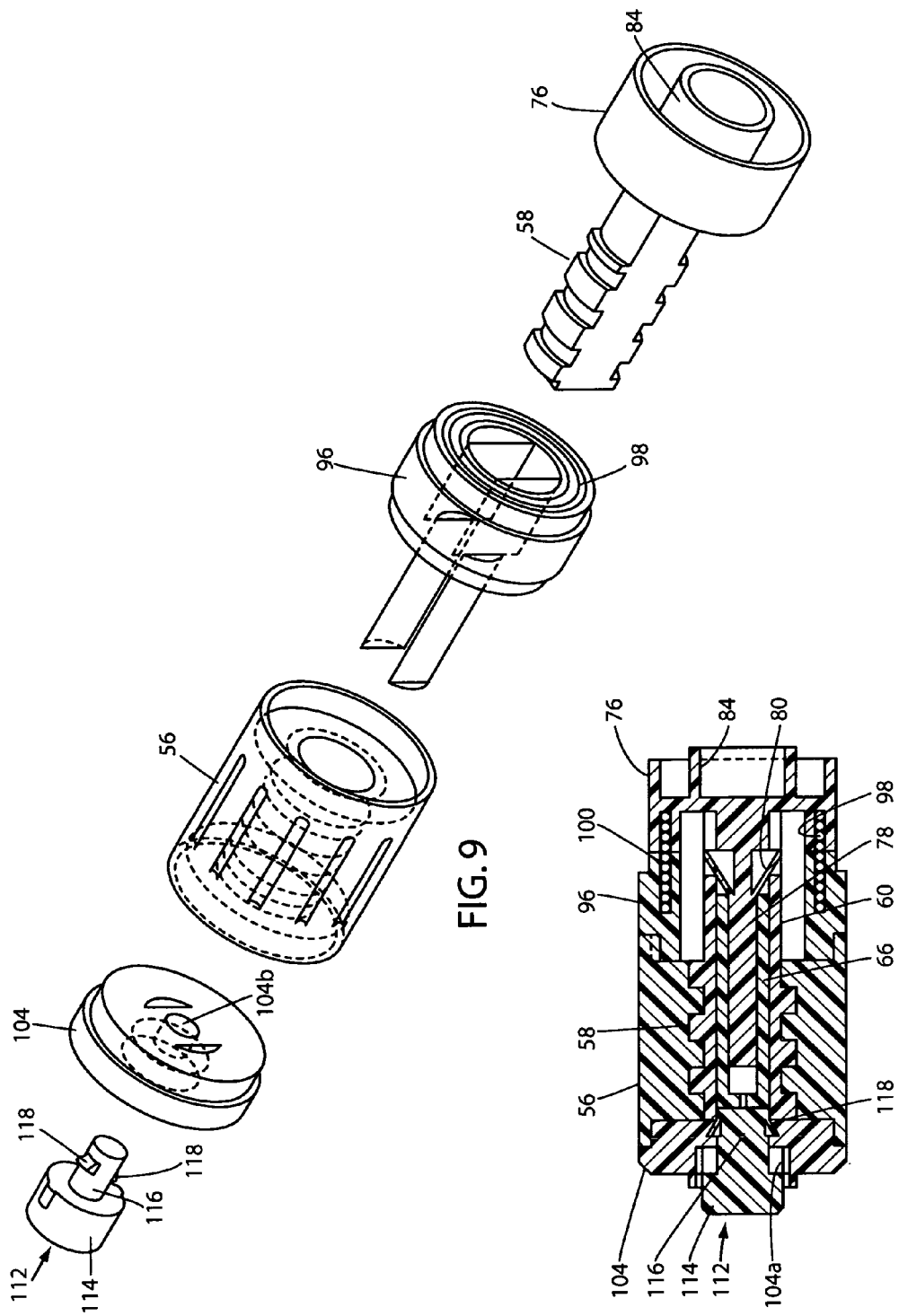

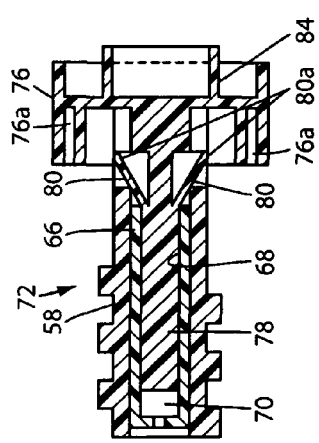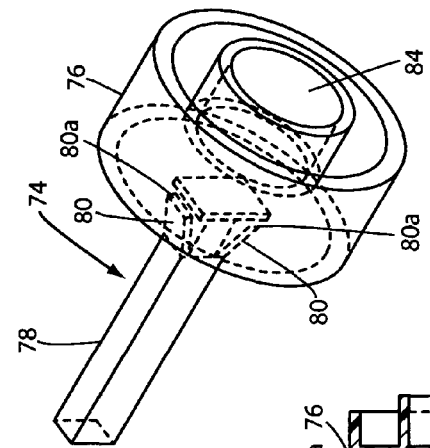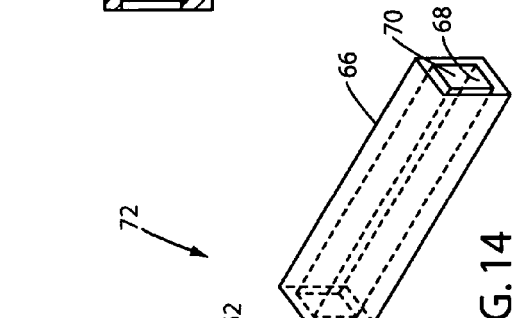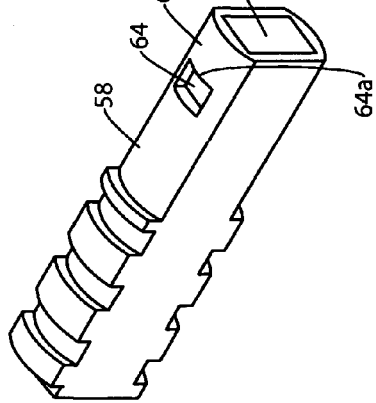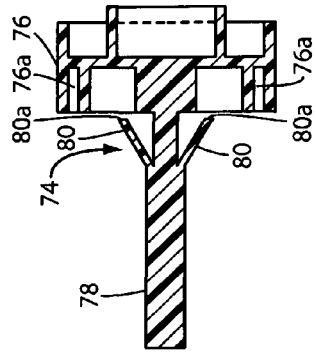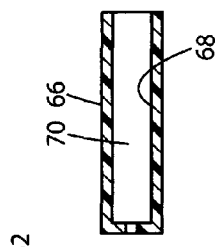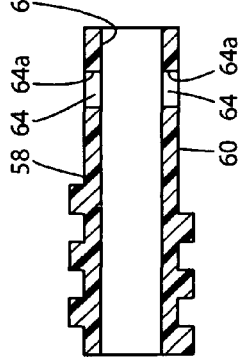
FIG. 13
FIG. 14
FIG. 15

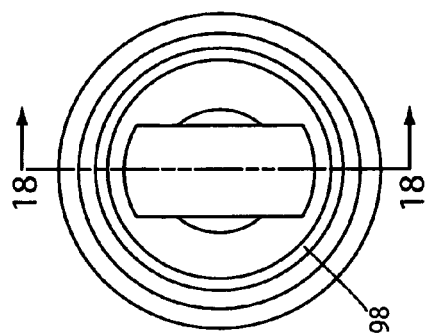
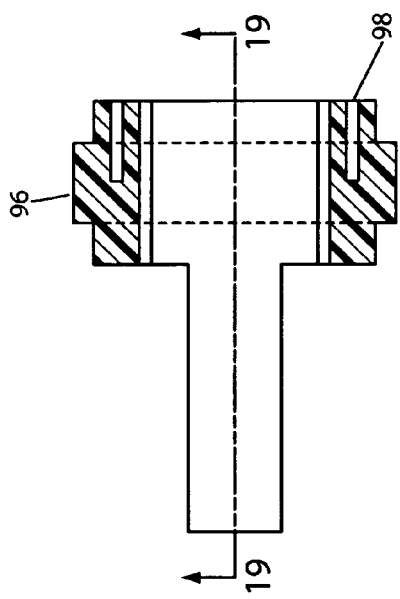
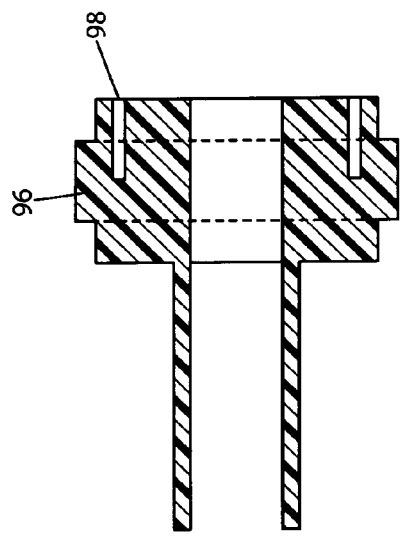
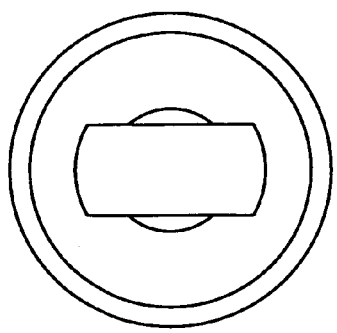
FIG. 17
FIG. 18
FIG. 19
FIG. 16

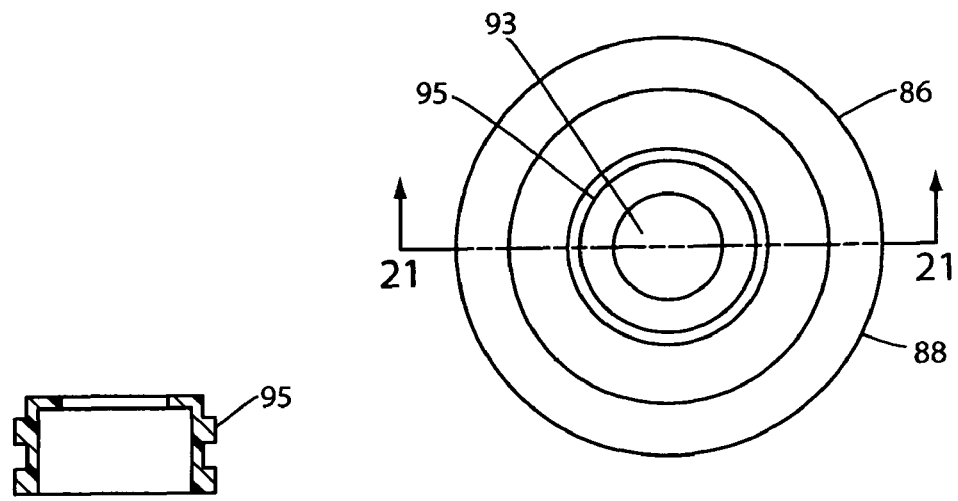
FIG. 20
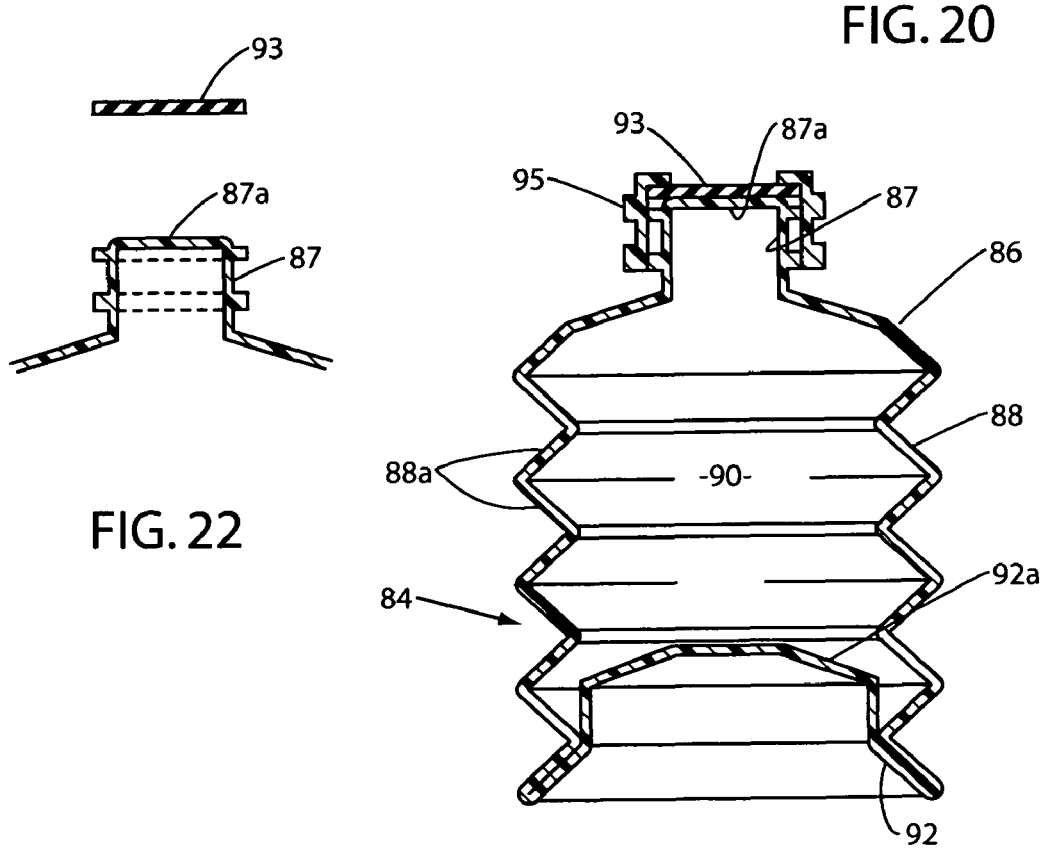
FIG. 22
FIG. 21

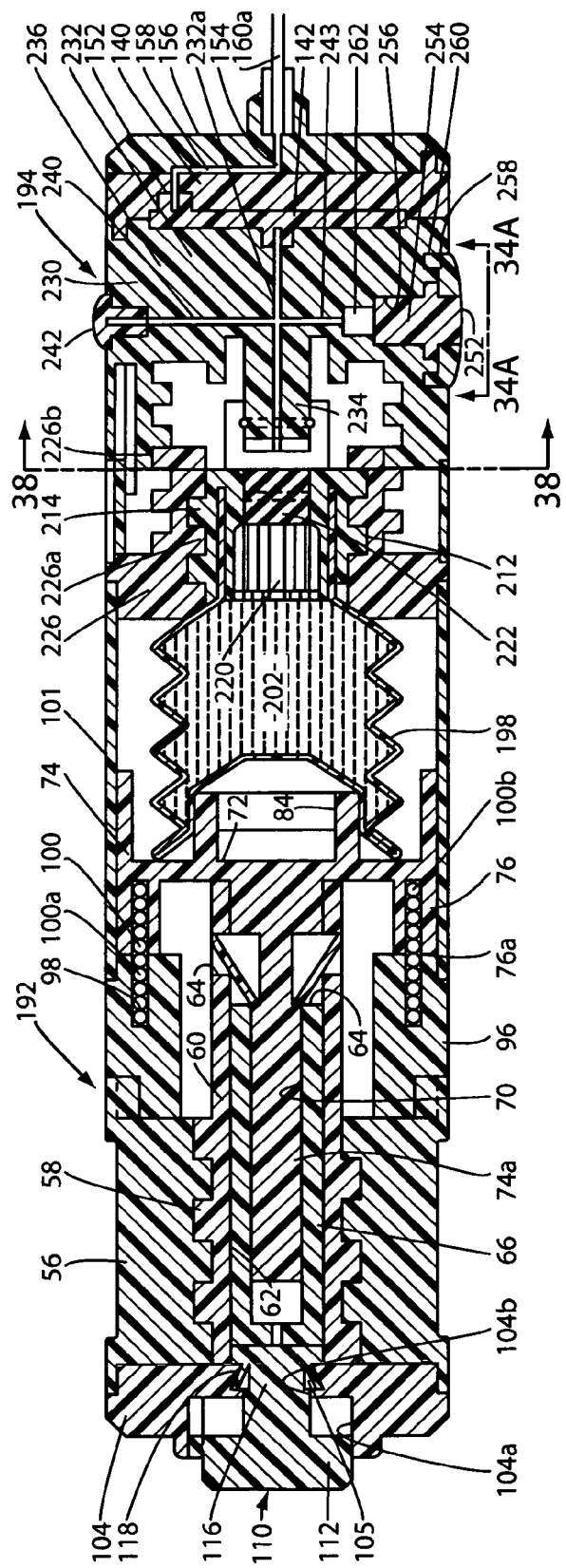
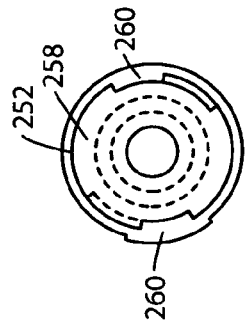
FIG. 34
FIG. 34A

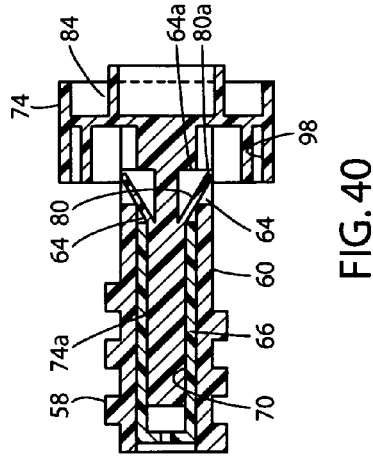
FIG. 40
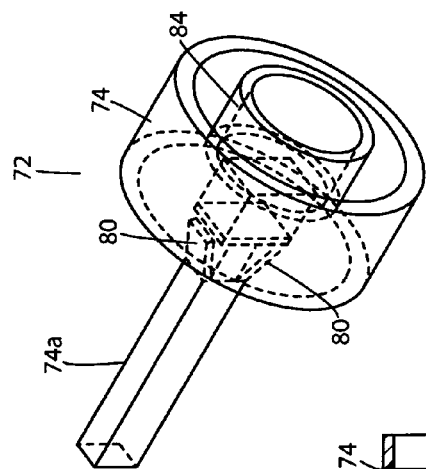
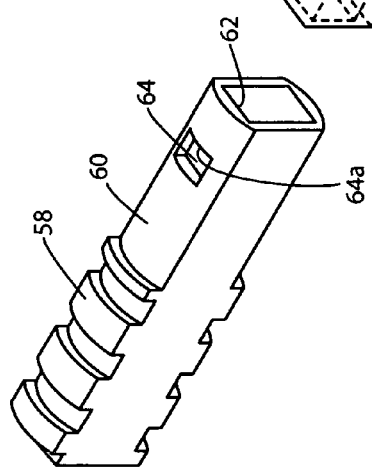
FIG. 41
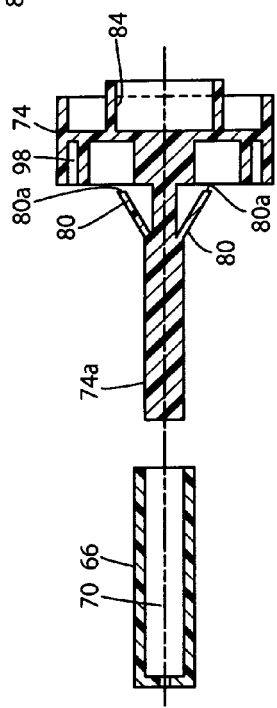
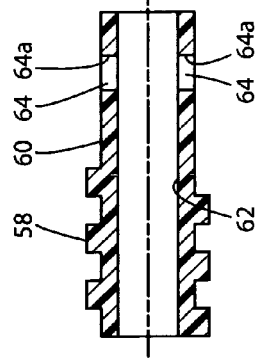
FIG. 42

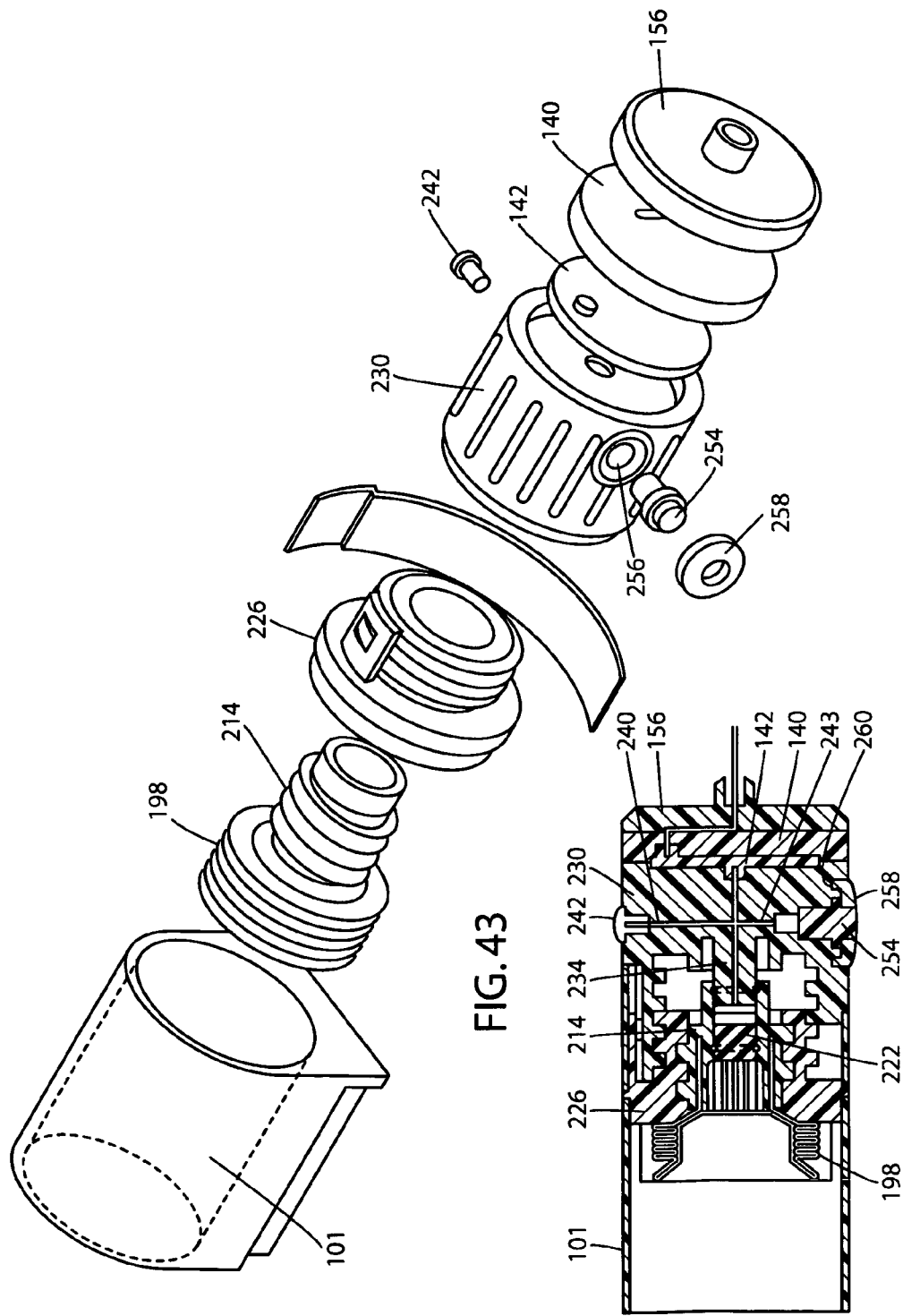

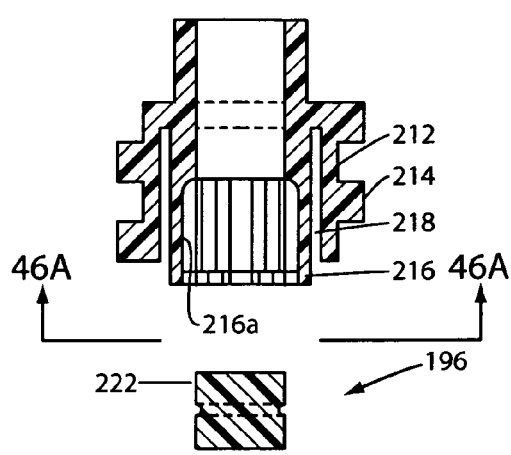
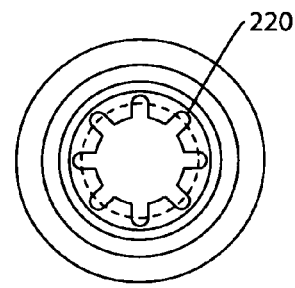
FIG. 46A
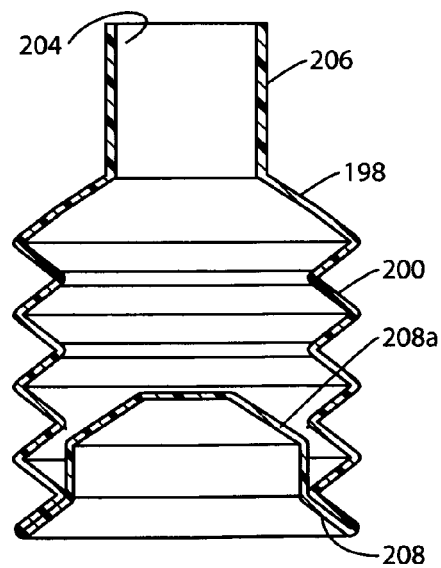
FIG. 46
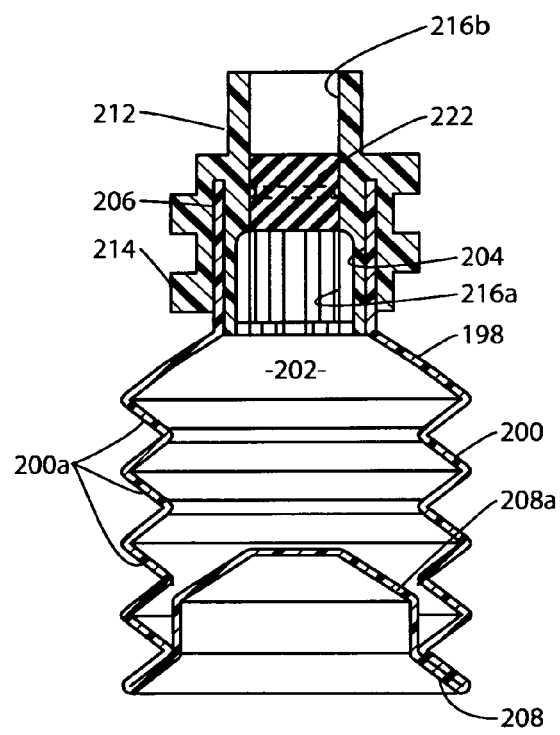
FIG. 45

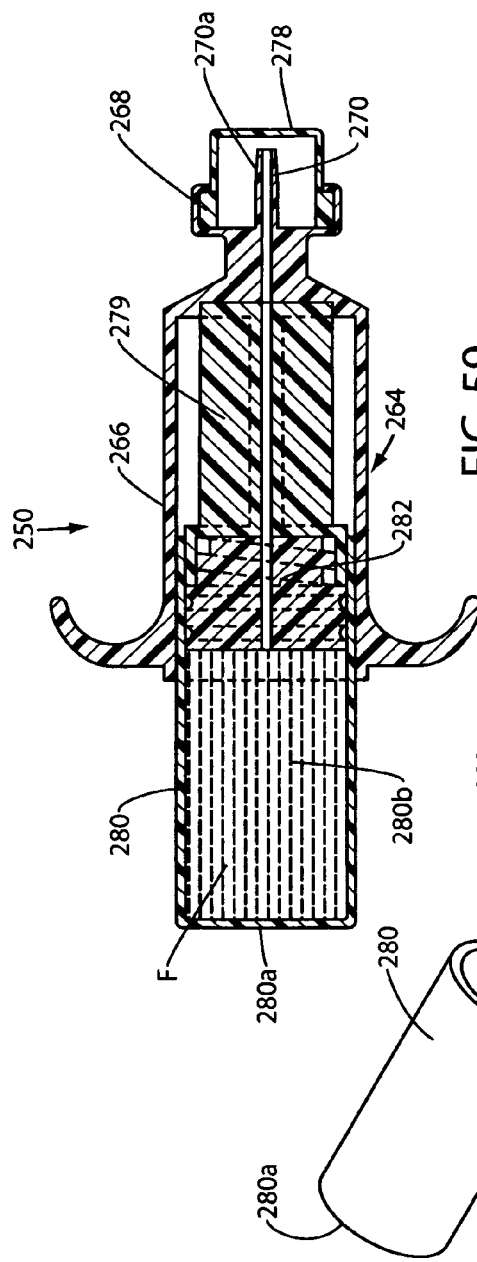
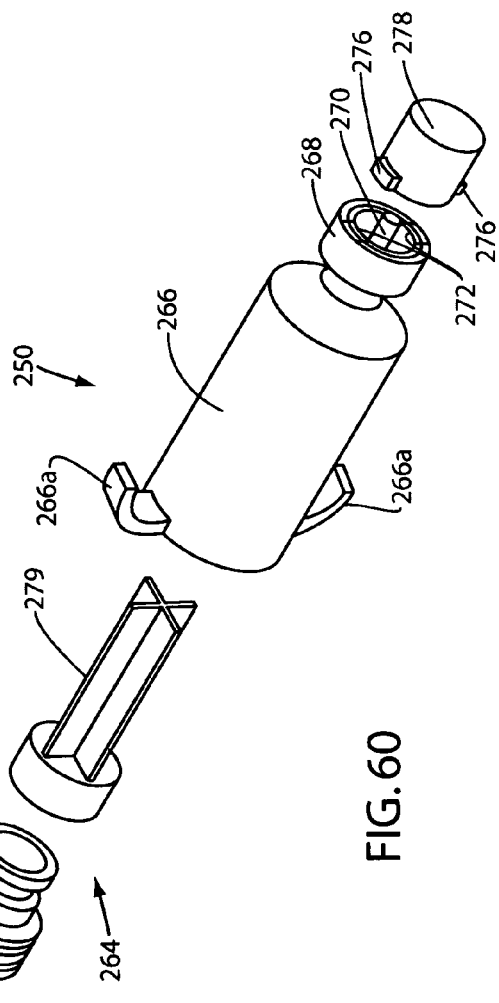
FIG. 59
FIG. 60

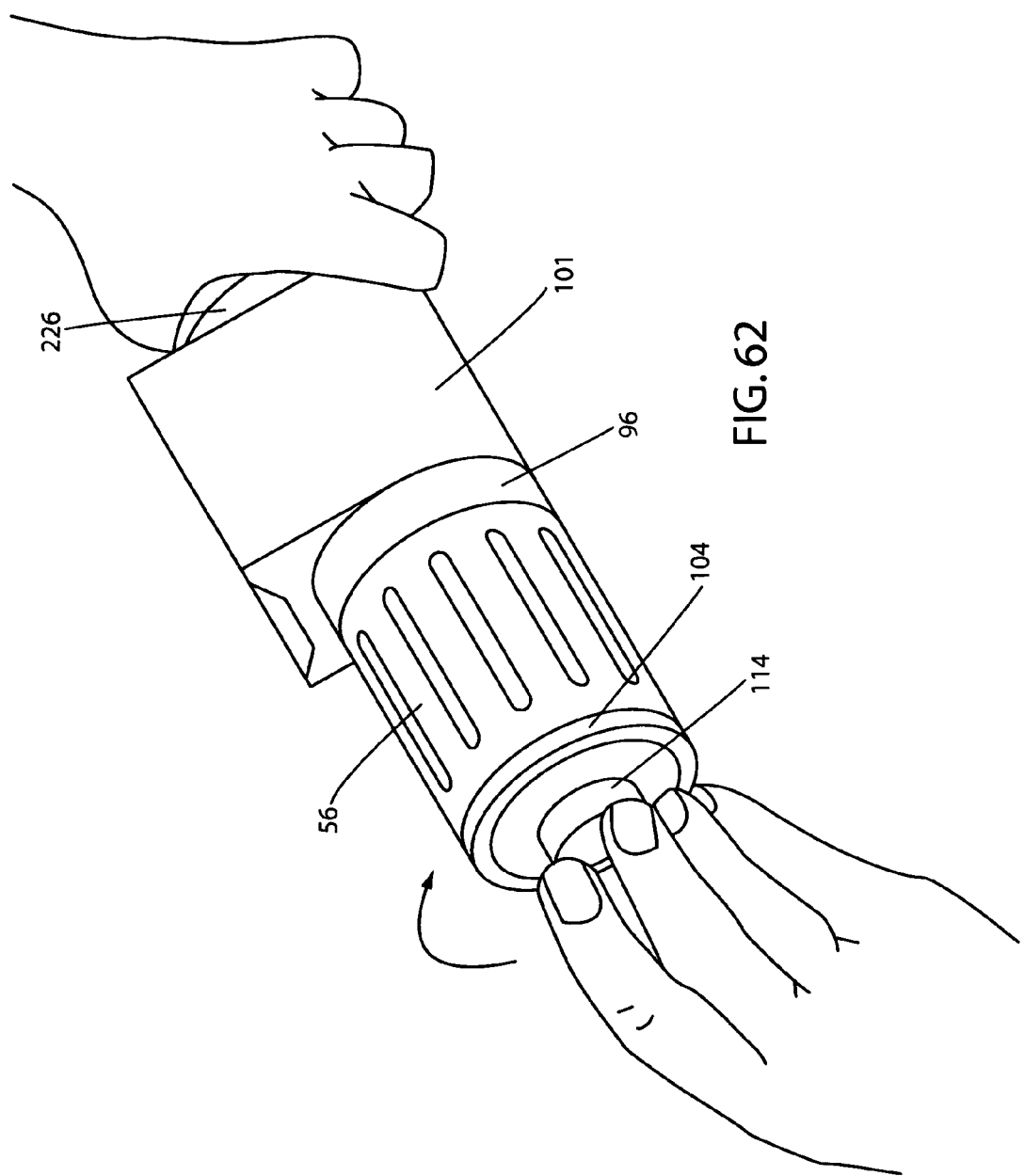

MEDICAMENT DISPENSER

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates generally to fluid dispensing devices. More particularly, the invention concerns a medicament dispenser of a simple, easy to use construction for dispensing medicinal fluids to ambulatory patients.

2. Description of Related Art Including Information Disclosed Under 37 CFR 1.97 and 1.98

A number of different types of medicament dispensers for dispensing medicaments to ambulatory patients have been suggested in the past. Many of the devices seek either to improve or to replace the traditional gravity flow and hypodermic syringe methods which have been the standard for delivery of liquid medicaments for many years.

With regard to the prior art, one of the most versatile and unique fluid delivery apparatus developed in recent years is that developed by the present inventor and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued to the present applicant, namely U.S. Pat. No. 5,743,879, discloses an injectable medicament dispenser for use in controllably dispensing fluid medicaments such as insulin, anti-infectives, analgesics, oncolylotics, cardiac drugs, bio-pharmaceuticals, and the like from a pre-filled container at a uniform rate. The dispenser, which is quite dissimilar in construction and operation from that of the present invention, includes a stored energy source in the form of a compressively deformable, polymeric, elastomeric member that provides the force necessary to controllably discharge the medicament from a pre-filled container which is housed within the body of the device. After having been deformed, the polymeric, elastomeric member will return to its starting configuration in a highly predictable manner.

A more recent fluid dispensing apparatus invented by the named inventor of the present application is disclosed in U.S. Pat. No. 7,220,245. This apparatus comprises a compact fluid dispenser for use in controllably dispensing fluid medicaments such as, antibiotics, oncolylotics, hormones, steroids, blood clotting agents, analgesics, and like medicinal agents from prefilled containers at a uniform rate. The dispenser uniquely includes a stored energy source that is provided in the form of a substantially constant-force, compressible-expandable wave spring that provides the force necessary to continuously and uniformly expel fluid from the device reservoir. The device further includes a fluid flow control assembly that precisely controls the flow of medicament solution to the patient.

BRIEF SUMMARY OF THE INVENTION

By way of brief summary, one form of the dispensing device of the present invention for dispensing medicaments to a patient comprises first and second operably associated assemblies. The first of these assemblies comprises a fluid reservoir sub-assembly that houses a carriage and a fluid reservoir defining component in the form of a collapsible container formed from a moldable plastic, while the second assembly comprises a fluid delivery and control sub-assembly that includes a novel flow control means that functions to control the flow of medicinal fluid from the fluid reservoir of the reservoir defining component toward the patient via a plurality of interconnected fluid flow control passageways.

With the forgoing in mind, it is an object of the present invention to provide a medicament dispenser of a simple, easy to use construction that can be used to dispense to the patient medicinal fluids such as antibiotics, anesthetics, analgesics, and like medicinal agents, at a uniform rate.

Another object of the invention is to provide a fluid dispensing apparatus of the aforementioned character that can effectively be used in the home care environment with a minimum amount of training.

Another object of the invention is to allow infusion therapy to be initiated quickly at the point of care without the assistance of a medical professional.

Another object of the invention is to provide a novel, medicament dispensing apparatus in which the fluid reservoir of the collapsible container is prefilled at time of manufacture.

Another object of the invention is to provide an alternate form of medicament dispensing device in which the fluid reservoir of the collapsible container can be filled in the field using a novel fill assembly.

Another object of the invention is to provide a dispenser of the class described which includes a fluid flow control assembly that precisely controls the flow of the medicament solution to the patient.

Another object of the invention is to provide a fluid dispensing apparatus of the character described in the preceding paragraphs that embodies an integrally formed, aseptically filled, unitary semi-rigid collapsible container that includes a fluid reservoir that contains the beneficial agents to be delivered to the patient.

Another object of the invention is to provide a fluid dispensing apparatus of the class described that is capable of administering a unit dose of medicament to the patient.

Another object of the invention is to provide a fluid dispensing apparatus of the class described which is compact and lightweight, is easy for ambulatory patients to use and is extremely reliable in operation.

Another object of the invention is to provide a fluid dispensing apparatus that is easy and inexpensive to manufacture in large quantities.

BRIEF DESCRIPTION OF SEVERAL VIEWS OF THE DRAWINGS

FIG. 1 is a generally perspective top view of one form of the fluid dispensing device of the present invention for dispensing medicaments to a patient.

FIG. 2 is a generally perspective bottom view of the outer housing of the dispensing device shown in FIG. 1.

FIG. 9 is a generally perspective, exploded view of the first sub-assembly, or rear portion of the dispensing device shown in FIG. 1.

FIG. 10 is a cross-sectional view of the first sub-assembly of the dispensing device shown in FIG. 9.

FIG. 13 is a cross-sectional view of the reservoir shuttle assembly of the dispensing device.

FIG. 14 is a generally perspective, exploded view of the reservoir shuttle assembly shown in FIG. 12.

FIG. 15 is a cross-sectional, exploded view of the reservoir shuttle assembly shown in FIG. 12.

FIG. 16 is a rear view of the spring base housing of the dispensing device.

FIG. 17 is a front view of the spring base housing shown in FIG. 16.

FIG. 18 is a cross-sectional view taken along lines 18-18 of FIG. 17.

FIG. 19 is a cross-sectional view taken along lines 19-19 of FIG. 18.

FIG. 20 is a top plan view of the collapsible container assembly of the dispensing device.

FIG. 21 is a cross-sectional view taken along lines 21-21 of FIG. 20.

FIG. 22 is a cross-sectional, exploded view of the upper portion of the collapsible container shown in FIG. 21.

FIG. 34 is a longitudinal cross-sectional view of the alternate form of the dispensing device as it appears following filling of the fluid reservoir.

FIG. 34A is a view taken along lines 34A-34A of FIG. 34.

FIG. 40 is a cross-sectional view of the reservoir shuttle assembly of the dispensing device.

FIG. 41 is a generally perspective, exploded view of the reservoir shuttle assembly shown in FIG. 40.

FIG. 42 is a cross-sectional, exploded view of the reservoir shuttle assembly shown in FIG. 41.

FIG. 43 is a generally perspective, exploded view of the first sub-assembly, or rear portion of the dispensing device shown in FIG. 32.

FIG. 44 is a cross-sectional view of the first sub-assembly of the dispensing device shown in FIG. 43.

FIG. 45 is a cross-sectional view of the collapsible container assembly of this latest form of the dispensing device.

FIG. 46 is a cross-sectional, exploded view of the collapsible container assembly shown in FIG. 45.

FIG. 46A is a view taken along lines 46A-46A of FIG. 46.

FIG. 59 is a longitudinal cross-sectional view of the reservoir fill assembly of the invention shown in FIG. 33A.

FIG. 60 is a generally perspective, exploded view of the reservoir fill assembly.

FIG. 62 is a generally perspective, diagrammatic view illustrating the second step in the operation of the apparatus of this latest form of the invention.

DETAILED DESCRIPTION OF THE INVENTION

Figure 3:
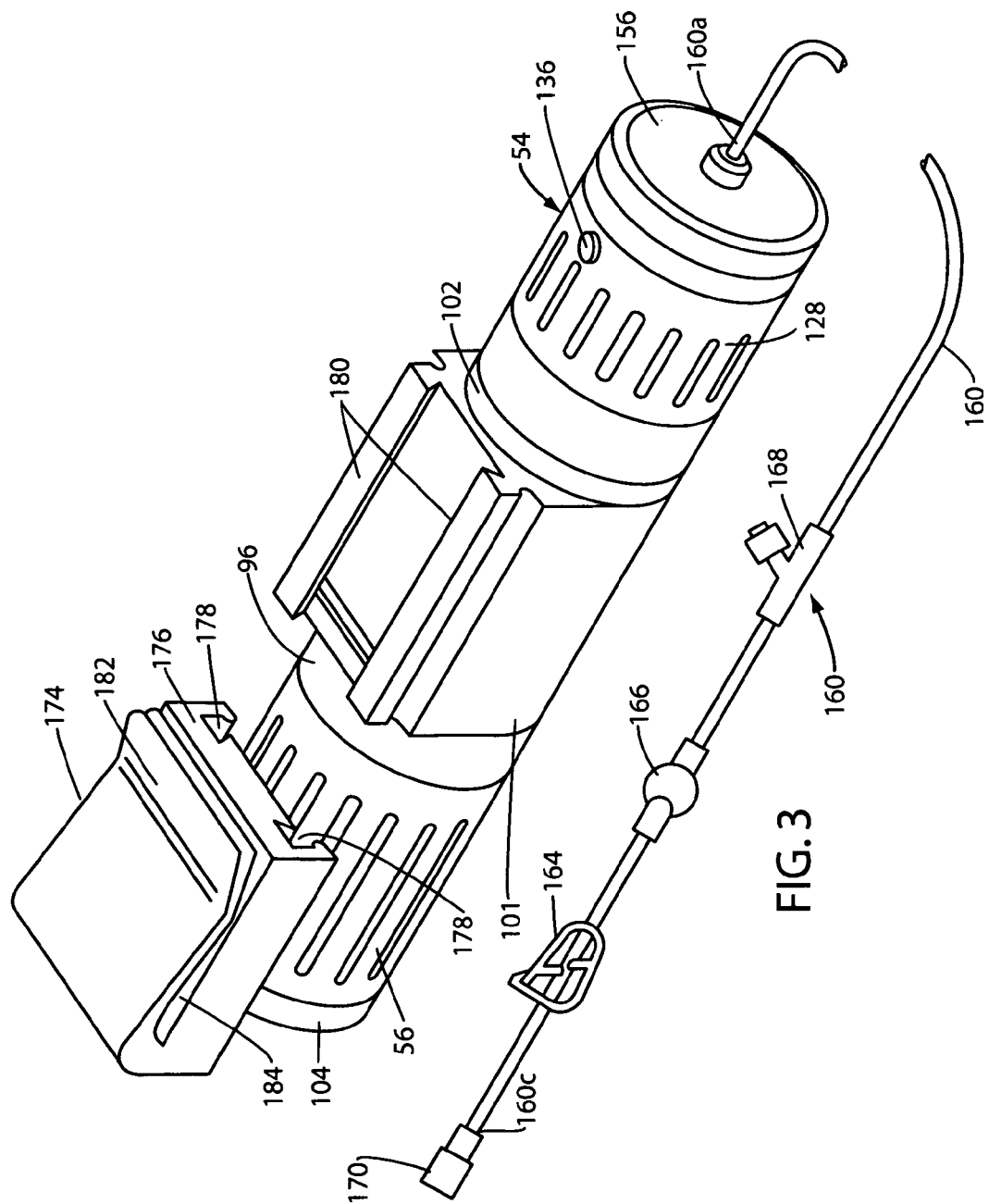
FIG. 3 is a generally perspective bottom view of the dispensing device illustrated in FIG. 1 showing in exploded view the belt clip of the apparatus.

Definitions—as Used Herein, the Following Terms have the Following Meanings:

Unitary Container:
A closed container formed from a single component.

Continuous/Uninterrupted Wall:
A wall having no break in uniformity or continuity.

Hermetically Sealed Container:
A container that is designed and intended to be secure against the entry of microorganisms and to maintain the safety and quality of its contents after pressurizing.

Beneficial Agent:
The term beneficial agent can include any substance or compound that is biologically active and includes any physiologically or pharmacologically active substance that produces a localized or systemic effect in humans or animals and that can be delivered by the present invention to produce a beneficial and useful result.

Reservoir:
A receptacle or chamber for storing a fluid. A part of a machine, apparatus, where liquid is stored.

Liquid Container:
A receptacle for holding a liquid. A fluid dispenser that is carried or transported.

Collapsible:
To cause to fold, or compress longitudinally in an accordion-like manner.

Collapsible Container:
A dispensing apparatus in which one or more walls of the container are made of a material which will deform (collapse) in an accordion-like manner when pressure is applied thereto; or alternatively, a dispensing apparatus having a collapsible or telescoping wall structure.

Aseptic Processing:
The term 'aseptic processing' as it is applied in the pharmaceutical industry refers to the assembly of sterilized components and product in a specialized clean environment.

Sterile Product:
A sterile product is one that is free from all living organisms, whether in a vegetative or spore state.

Blow-Fill-Seal Process:
The concept of aseptic blow-fill-seal (BFS) is that a container is formed, filled, and sealed as a unitary container in a continuous manner without human intervention in a sterile enclosed area inside a machine. The process is multi-stepped, pharmaceutical grade resin is extruded into a tube, which is then formed into a container. A mandrel is inserted into the newly formed container and filled. The container is then sealed, all inside a sterile shrouded chamber. The product is then discharged to a non-sterile area for packaging and distribution.

Integrally Formed:
An article of one-piece construction or several parts that are rigidly secured together and is smoothly continuous in form and that any such components making up the part have been then rendered inseparable.

Frangible:
An article, item or object that is capable of being ruptured or broken, but does not necessarily imply any inherent materials weakness. A material object, under load that demonstrates a mechanical strain rate deformation behavior, leading to disintegration.

Luer-Like Connector:
A connector used to connect medical apparatus. Classically, the Luer consists of a tapered barrel and a conical male part that fits into it with or without a seal.

Spring:
A mechanical element that can be deformed by a mechanical force such that the deformation is directly proportional to the force or torque applied to it. An elastic machine component able to deflect under load in a prescribed manner and to recover its initial shape when unloaded. The combination of force and displacement in a deflected spring is energy which may be stored when moving loads are being arrested.

Unit Dose:
As used herein, "unit dose" means the amount of a medication administered to a patient in a single dose.

Figure 4:
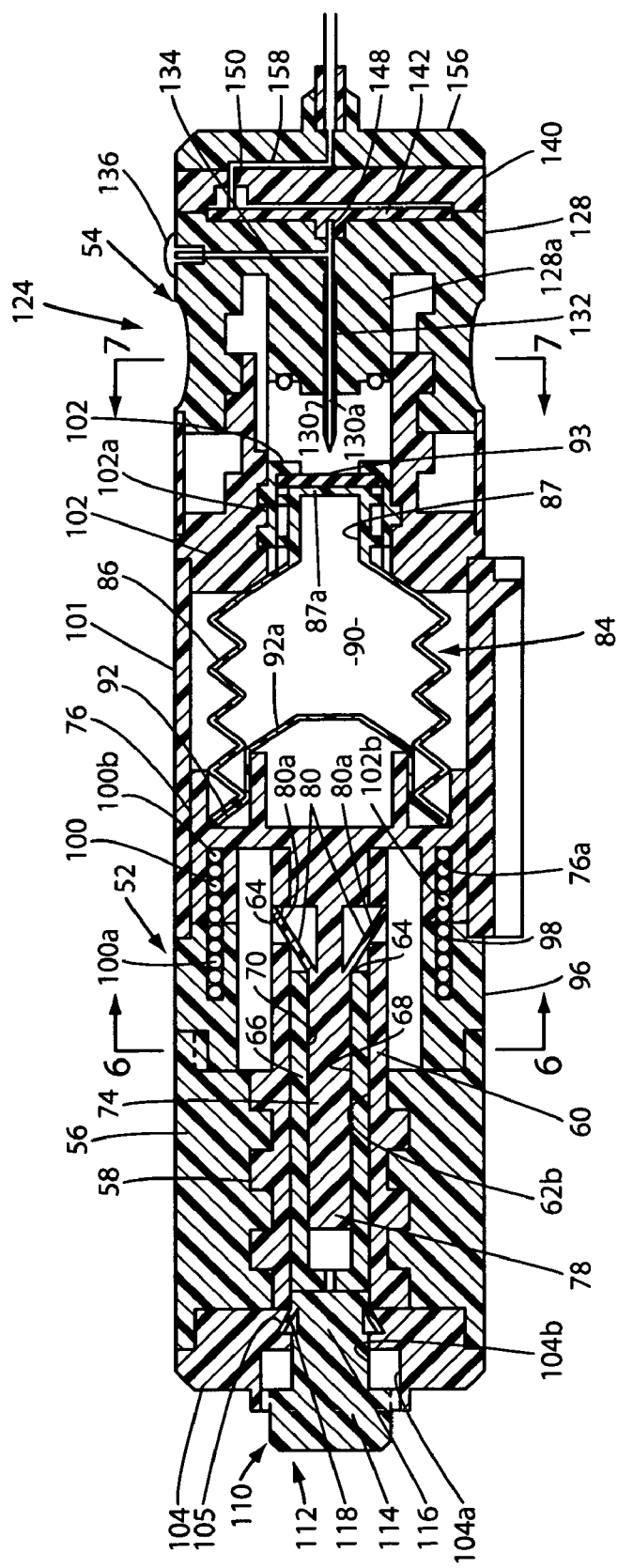
FIG. 4 is an enlarged, longitudinal cross-sectional view of the dispensing device shown in FIG. 1.

Referring to the drawings and particularly to FIGS. 1 through 3, one form of the fluid dispensing apparatus of the present invention for dispensing medicaments to a patient is there shown and generally designated in FIG. 1 by the numeral 50. The dispensing apparatus here comprises first and second operably associated assemblies 52 and 54. As best seen in FIG. 4 of the drawings, first assembly 52 comprises an internally threaded first housing 56 and an externally threaded shuttle housing 58 that is threadably connected to first housing 56 in the manner shown in FIG. 4 of the drawings. Shuttle housing 58 has an exterior wall 60 defining an axial passageway 62. For a purpose presently to be described, external wall 60 is provided with a pair of oppositely disposed openings 64 (see FIGS. 14 and 15).

Figure 5:
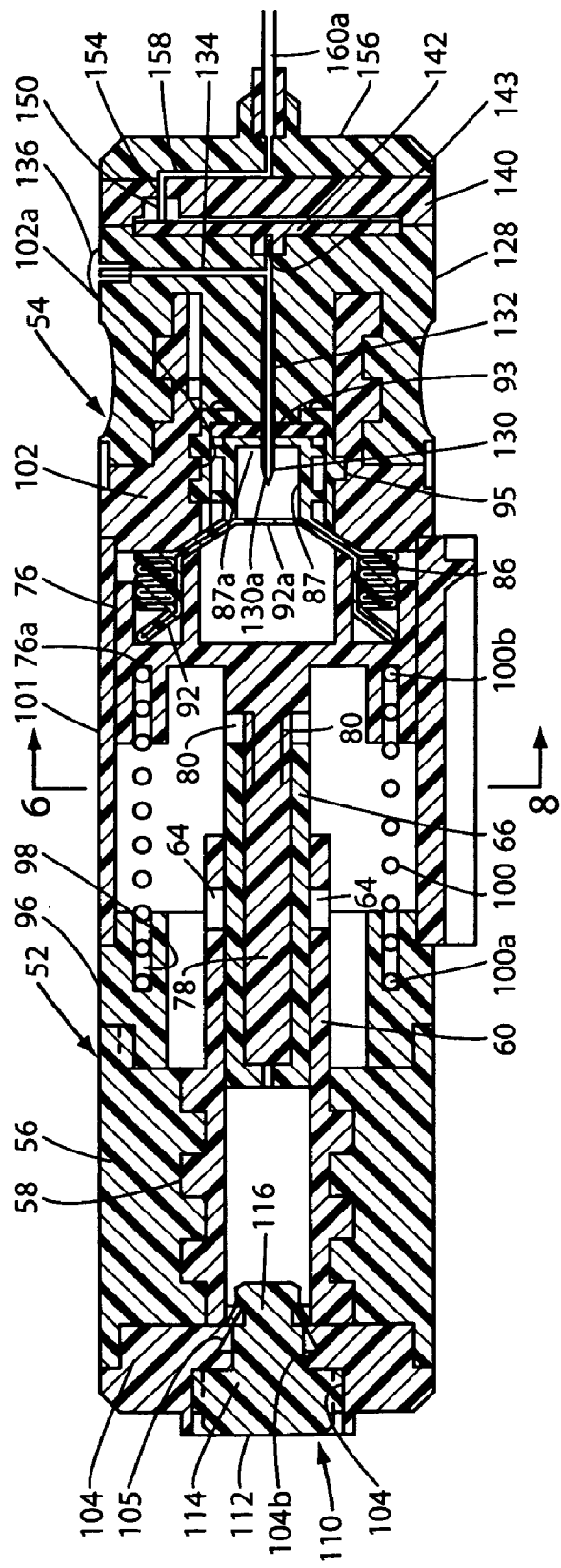
FIG. 5 is an enlarged, longitudinal cross-sectional view similar to FIG. 4, but showing the device as it appears after the medicaments have been dispensed to the patient.

Mounted within the axial passageway 62 of the shuttle housing for movement between a first retracted position shown in FIG. 4 and a second advanced position shown in FIG. 5 is a shuttle 66. Shuttle 66 has an inner wall 68 that defines an axial passageway 70. Operably associated with shuttle 66 is a carriage assembly 72 that includes a carriage 74 that is movable within axial passageway 70 between a first position shown in FIG. 4 and a second position shown in FIG. 5.

As best seen in FIGS. 4, 10 and 15, carriage 74 includes a generally cylindrical head portion 76 and a shank portion 78 that is uniquely provided with a pair of outwardly extending, yieldably deformable locking wings 80.

Locking wings 80 comprise the locking means of the invention for locking the carriage in its first position. As indicated in FIGS. 4 and 13, the end portions 80a of the locking wings extend through the openings 64 provided in shuttle housing 58 and in the carriage lock position shown in FIG. 4 and engage the forward walls 64a of the openings so as to prevent movement of the carriage 74 between its first position shown in FIG. 4 and its second position shown in FIG. 5.

Carried by carriage 74 is a reservoir assembly 84 that comprises a unitary pre-filled collapsible container 86. More particularly, as illustrated in FIG. 4 of the drawings, the bottom portion of the collapsible container 86 is received between the cylindrical head portion 76 of carriage 74 and a concentric, smaller diameter cylindrical portion 84.

As best seen in FIG. 21 of the drawings, unitary pre-filled collapsible container 86 has a continuous accordion-shaped side wall 88 formed of a single material that defines a hermetically sealed collapsible reservoir 90 that has an outlet 92a and contains the medicinal fluid "F" to be delivered to the patient. The accordion-shaped side wall 88 comprises a multiplicity of adjacent generally "V" shaped interconnected folds 88a. In the preferred form of the invention, reservoir 90 is aseptically filled and sealed at time of manufacture. Collapsible container 86 has a neck portion 87 having a closure wall 87a. For a purpose presently to be described, the continuous wall 88 of the collapsible container also uniquely includes an end wall 92 having an inwardly extending ullage defining protuberance 92a. Reservoir assembly 84 also includes a pierceable membrane 93 that is superimposed over closure wall 87a and a closure cap 95 that is affixed to neck portion 87 (see FIG. 22).

Pre-filled collapsible container 86 is constructed in accordance with aseptic blow-fill seal manufacturing techniques, the character of which is well understood by those skilled in the art. Basically, this technique involves the continuous plastic extrusion through an extruder head of a length of parison in the form of a hollow tube between and through two co-acting first or main mold halves. The technique further includes the step of cutting off the parison below the extruder head and above the main mold halves to create an opening which allows a blowing and filling nozzle assembly to be moved downwardly into the opening in the parison for molding and then filling the molded container in a sterile fashion. Following the molding, filling and sealing of the container, it is sterilized at high temperature in a manner well understood by those skilled in the art. Unlike chemical or gamma ray sterilization, this temperature sterilization step has no adverse effect on the medicament contained within the container reservoir.

More particularly, it is important that as much of the beneficial agents contained within the collapsible container 86 be dispensed from a container in a proper predetermined unit dose, following protocol, to avoid improper dosage, waste and undue expense. Accordingly, the previously identified ullage defining protuberance 92a functions to fill the interior space of the collapsible container when it is collapsed in the manner shown in FIG. 5 of the drawings.

Interconnected with first housing 56 is a spring housing 96 having a circumferentially extending spring cavity 98 that receives the rear portion 100a of a coil spring 100. Spring 100 comprises the stored energy means of the invention for moving the carriage from its first position to its second position. Spring 100 is operably associated with the carriage 74 in the manner shown in FIG. 4 and, when the carriage is released from its locked position by operation of the locking means, functions to move the carriage from its first position to its second position. More particularly, the generally cylindrical head portion 76 of the carriage 74 includes a circumferentially extending spring cavity 76a that receives the forward portion 100b of a coil spring 100 so that the spring can act directly on the carriage.

Connected to spring housing 96 and forming a part of the first assembly 52 is a reservoir housing 101. Reservoir housing 101 interconnects spring housing 96 with an internally-externally threaded reservoir securement member 102. The internally threaded portion 102a of the reservoir securement member threadably engages the externally threaded neck portion 87 of the collapsible container so as to securely hold it in position within the device in the manner illustrated in FIG. 4 of the drawings Connected to first housing 56 is a base member 104 that is provided with a first bore 104a of a first diameter and a second bore 104b of a second, lesser diameter. Second bore 104b includes a circumferentially extending groove 105, the purpose of which will presently be described. Rotatably mounted within bores 104a and 104b for movement between a first retracted position shown in FIG. 4 and a second advanced position shown in FIG. 5 is a carriage release assembly 110. In a manner presently to be described, carriage release assembly 110 is operably associated with the locking means of the invention for acting on the locking means to release the carriage 74 from its locked position. Carriage release assembly 110 comprises a release member 112 having a finger engaging head portion 114 that is receivable within bore 104 and a shank portion 116 that is receivable within bore 106 and is disposed in engagement with shuttle 66 (FIG. 4). Shank portion 116 is provided with oppositely disposed, outwardly extending, yieldably deformable locking tabs 118 that are receivable within the circumferentially extending groove 106 of the second bore 106 in base 102.

Considering now the second assembly 54 of the dispensing apparatus, which is operably associated with first assembly 52, this important second assembly here comprises a novel fluid flow control means for controlling the flow of medicinal fluid toward the patient. The fluid flow control means here comprises two cooperating assemblies, namely a rate control assembly 122 for controlling the rate of fluid flow toward the patient and an operating assembly 124 for controlling the fluid flow between the device reservoir and the rate control assembly.

Figures 11, 12:
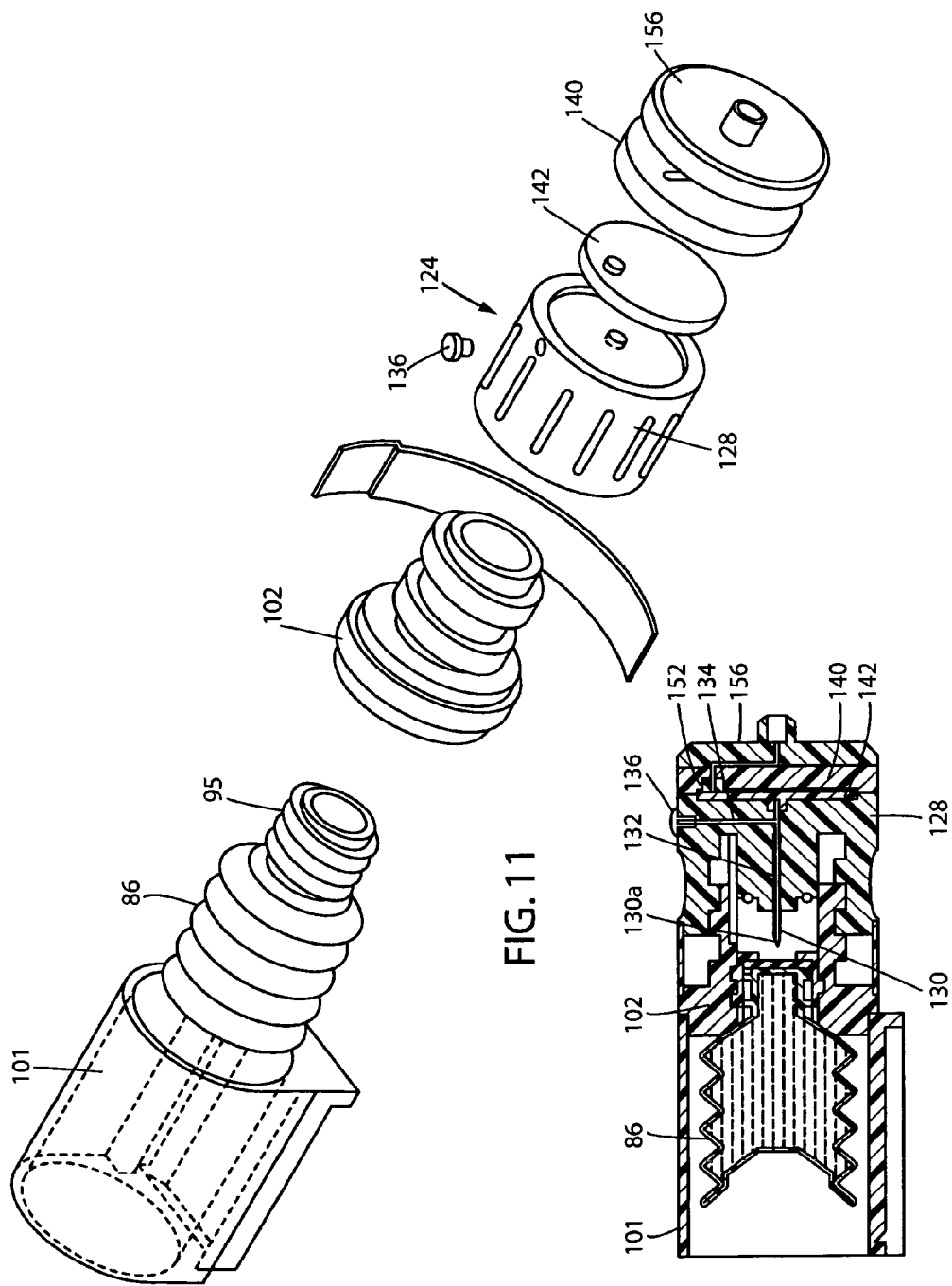
FIG. 11 is a generally perspective, exploded view of the second sub-assembly, or forward portion of the dispensing device shown in FIG. 1.
FIG. 12 is a cross-sectional view of the second sub-assembly of the dispensing device shown in FIG. 5.
Figure 23:
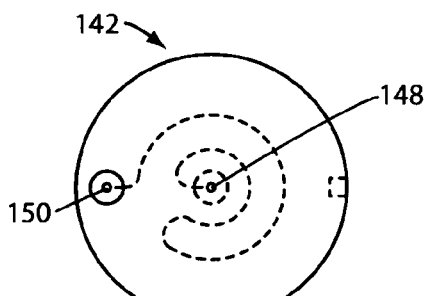
FIG. 23 is a front view of the rate control unit of the dispensing device that includes a rate control plate and a rate control plate cover.
Figure 25:
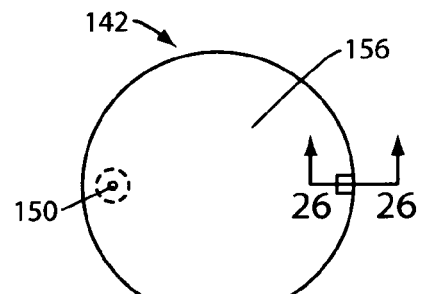
FIG. 25 is a view taken along lines 25-25 of FIG. 24 showing the rate control cover.

As best seen in FIGS. 4, 11 and 12, the operating assembly 124 includes an externally threaded piercing assembly 128 that includes a piercing member 130 having a fluid flow passageway 130a (FIG. 12). The fluid flow passageway 130a of the piercing member communicates with a longitudinally extending central fluid passageway 132 formed in the body portion 128a of the piercing assembly 128. Connected to the fluid passageway 132 and communicating therewith is a vent passageway 134 that, in turn, communicates with a gas vent port 136 formed in the body portion 128a.

Figure 26:
FIG. 26 is a cross-sectional view taken along lines 26-26 of FIG. 25.
Figure 24:
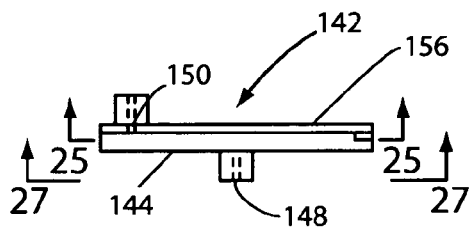
FIG. 24 is a side elevational view of the rate control unit of the dispensing device.
Figure 27:
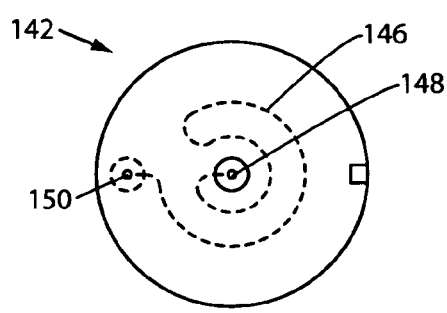
FIG. 27 is a view taken along lines 27-27 of FIG. 24 showing the rate control plate of the rate control unit.
Figure 28:
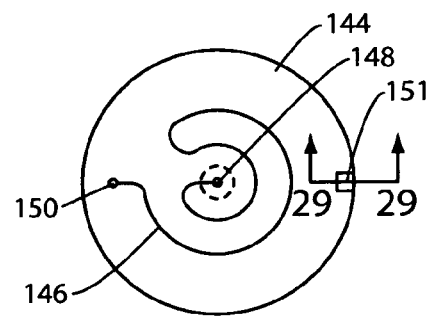
FIG. 28 is a front view of the rate control plate shown in FIG. 27.
Figure 29:
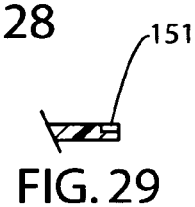
FIG. 29 is a cross-sectional view taken along lines 29-29 of FIG. 28.

Connected to piercing assembly 128 in the manner illustrated in FIG. 4 of the drawings is the important rate control means for controlling the rate of fluid flow from reservoir 90 toward the patient. The important rate control means of the invention here comprises a rate control housing 140 that houses the rate control assembly 142 of the invention (FIG. 24). As best seen by referring to FIGS. 23 through 29, rate control assembly 142 here includes a generally planar shaped rate control plate 144 which, as shown in FIG. 28, is provided with a serpentine micro-channel 146 having an inlet 148 and an outlet 150. The rate control plate is also provided with an indexing notch 151 (see FIG. 29). The outlet 150 of the micro channel, which is controllably etched into rate control plate 144, communicates with an outlet port 152 formed in rate control housing 140 and with an outlet passageway 154 formed in a forward closure member 156 which is provided with an indexing element 157 that mates with indexing notch 151 (see FIGS. 24 and 26). Outlet passageway 154, in turn, communicates with a longitudinally extending outlet passageway 158 formed in closure member 156. As best seen in FIGS. 3 and 5 of the drawings, outlet passageway 158 communicates with the administration line 160a of the administration set 160 of the apparatus.

As illustrated in FIG. 3 of the drawings, disposed between the proximal end 160b and the distal end 160c of the administration line are a conventional clamp 164, a conventional gas vent and filter 166, and a generally Y-shaped injector site, generally designated by the numeral 168. A luer connector 170 of conventional construction is provided at the distal end of the administration line for use in a conventional manner.

Figure 30:
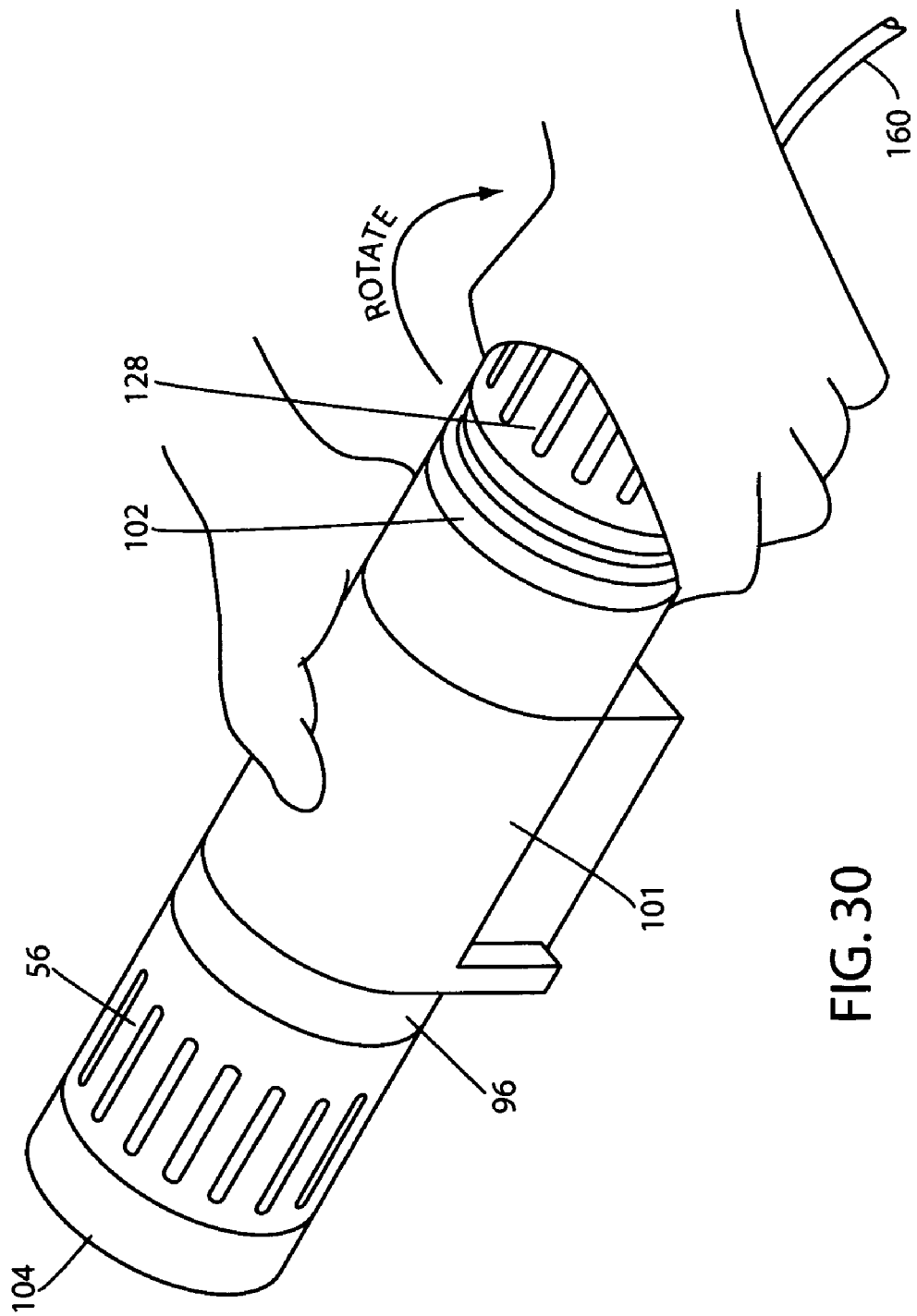
FIG. 30 is a generally perspective, diagrammatic view illustrating the first step in the operation of the apparatus.

In using the apparatus of the present form of the invention with the apparatus in the manufactured condition illustrated in FIG. 4 of the drawings, wherein the spring 100 is compressed and the carriage is locked in its retracted position by the yieldably deformable locking tabs 118, the first step in the operation of the apparatus involves the rotation of the internally threaded piercing assembly 128 relative to the internally-externally threaded reservoir securement member 102 in the manner illustrated in FIG. 30 of the drawings. As the piercing assembly 128 advances toward position shown in FIG. 5 of the drawings, the piercing member 130 will pierce the pierceable membrane 93 and the closure wall 87a of the collapsible container 86, thereby opening communication between the fluid passageway 130a of the piercing member and the fluid reservoir 90 of the collapsible container.

Figure 7:
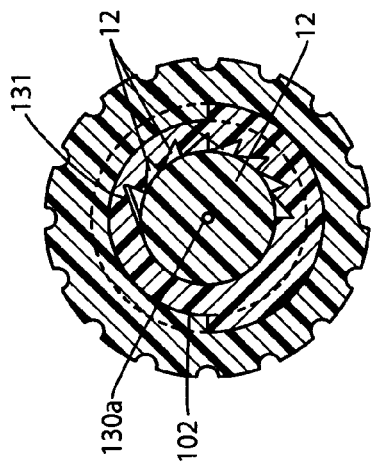
FIG. 7 is a cross-sectional view taken along lines 7-7 of FIG. 4.

As illustrated in FIG. 7, a portion of the inner wall of the reservoir securement member 102 is provided with a plurality of tooth-like cavities 129t. As the piercing assembly is rotated, an inwardly extending tab 131 provided on the piercing assembly rides over tooth-like cavities and permits rotation of the piercing assembly in one direction, but positively prevents its rotation in the opposite direction. With this construction, accidental reverse rotation of the piercing assembly is positively prevented.

Figure 31:
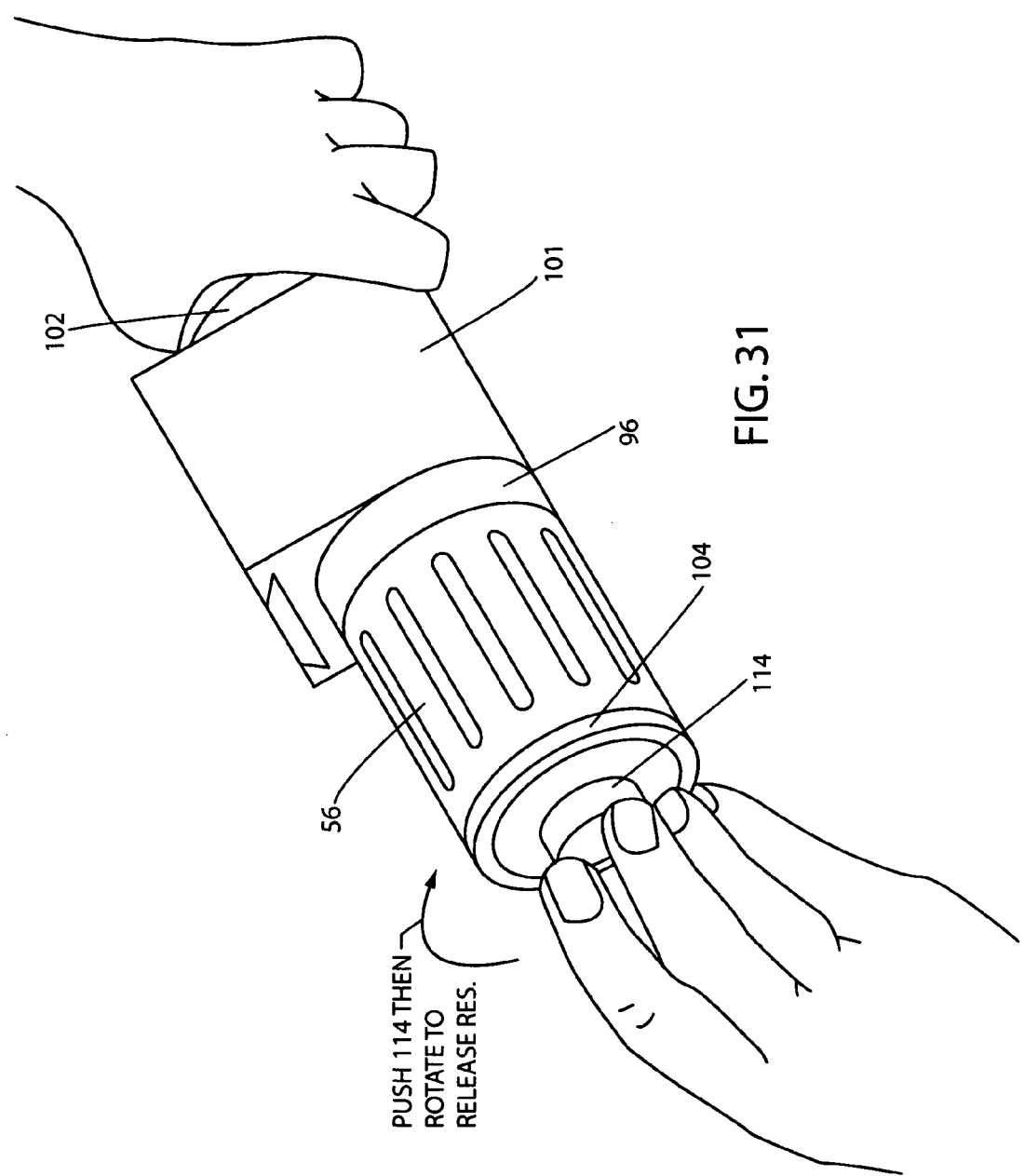
FIG. 31 is a generally perspective, diagrammatic view illustrating the second step in the operation of the apparatus.

With communication opened between the fluid passageway 130a of the piercing member and the fluid reservoir 90, the next step in the operation of the apparatus of the invention involves the manipulation of the carriage release assembly 110 to release the carriage from its locked position. This is accomplished in the manner illustrated in FIG. 31 of the drawings by first gripping the finger engaging head portion 114 of the release member 112 and rotating it to the position shown in FIG. 5 of the drawings wherein it can be pushed inwardly of bores 104a and 104b. As the release member is pushed inwardly, the shank portion 116 thereof engages the shuttle 66 and urges it forwardly into the position shown in FIG. 5 of the drawings. As the shuttle 66 moves forwardly, the yieldably deformable locking tabs 118 will be urged inwardly into the flattened position shown in FIG. 5, thereby releasing the carriage 74 from its locked position.

Figure 6:
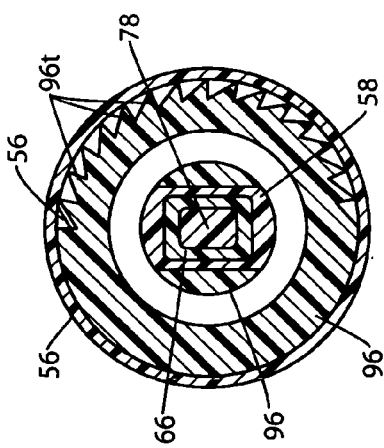
FIG. 6 is a cross-sectional view taken along lines 6-6 of FIG. 4.

As illustrated in FIG. 6, a portion of the circumference of spring housing 96 is provided with a plurality of tooth-like protuberances 96t. As housing 56 is rotated, a resiliently deformable, inwardly extending tab 59 provided on housing 56 rides over the tooth-like protuberances and permits rotation of the housing in one direction, but positively prevents its rotation in the opposite direction. With this construction, accidental reverse rotation of the housing is positively prevented.

Upon release of the carriage assembly as a result of the inward movement of the release member 112, the stored energy means, or spring 100, will move the carriage from its locked position shown in FIG. 4 into the advanced position shown in FIG. 5 and in so doing will collapse the reservoir defining component, or hermetically sealed container 86. As container 94 collapses, the fluid contained within reservoir 104 will flow toward penetrating member 130, into passageway 130a formed in the penetrating member and toward the rate control means of the invention. More particularly, from the fluid flow passageway 130a, the fluid will flow into the longitudinally extending central fluid passageway 132 formed in the body portion 128a of the piercing assembly 128 and then into the inlet 148 of the serpentine micro-channel 146. The fluid will flow through the micro-channel 148 at a controlled rate depending upon the depth, width and length of the micro-channel and outwardly of the micro-channel outlet 150. From outlet 150 medicinal fluid will flow from the outlet port 152 formed in rate control housing 140 and into the outlet passageway 154 formed in a forward closure member 156. From outlet passageway 154, the fluid will flow into longitudinally extending outlet passageway 158 and onward to the patient via the administration set of the apparatus.

Figure 8:
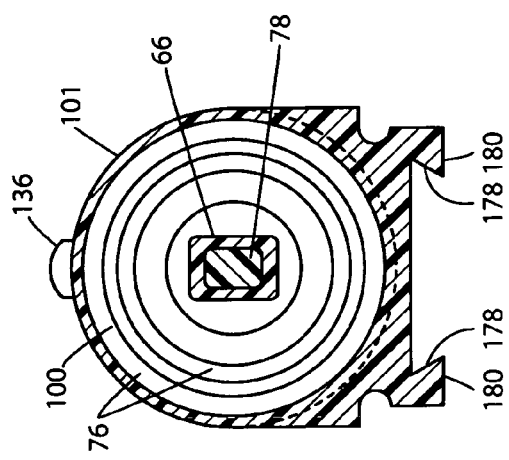
FIG. 8 is a cross-sectional view taken along lines 8-8 of FIG. 5.

As best seen by referring to FIG. 3 of the drawings, the dispensing device further includes a belt clip 174 that can be affixed to the reservoir housing 101 of the device so that, if desired, the device can be carried on the belt of the user. More particularly, belt clip 174 includes a base portion 176 having a pair of spaced apart dovetail grooves 178 that slidably receive dovetail rails 180 provided on the reservoir housing 101 (see also FIG. 8). Belt clip 174 also includes a yieldably deformable flap portion 182 that is connected to base portion 176 and cooperates therewith to define a belt receiving passageway 184. With the construction thus described, the belt clip can readily be connected to the reservoir housing and can be disconnected there from as may be desired.

Figure 32:
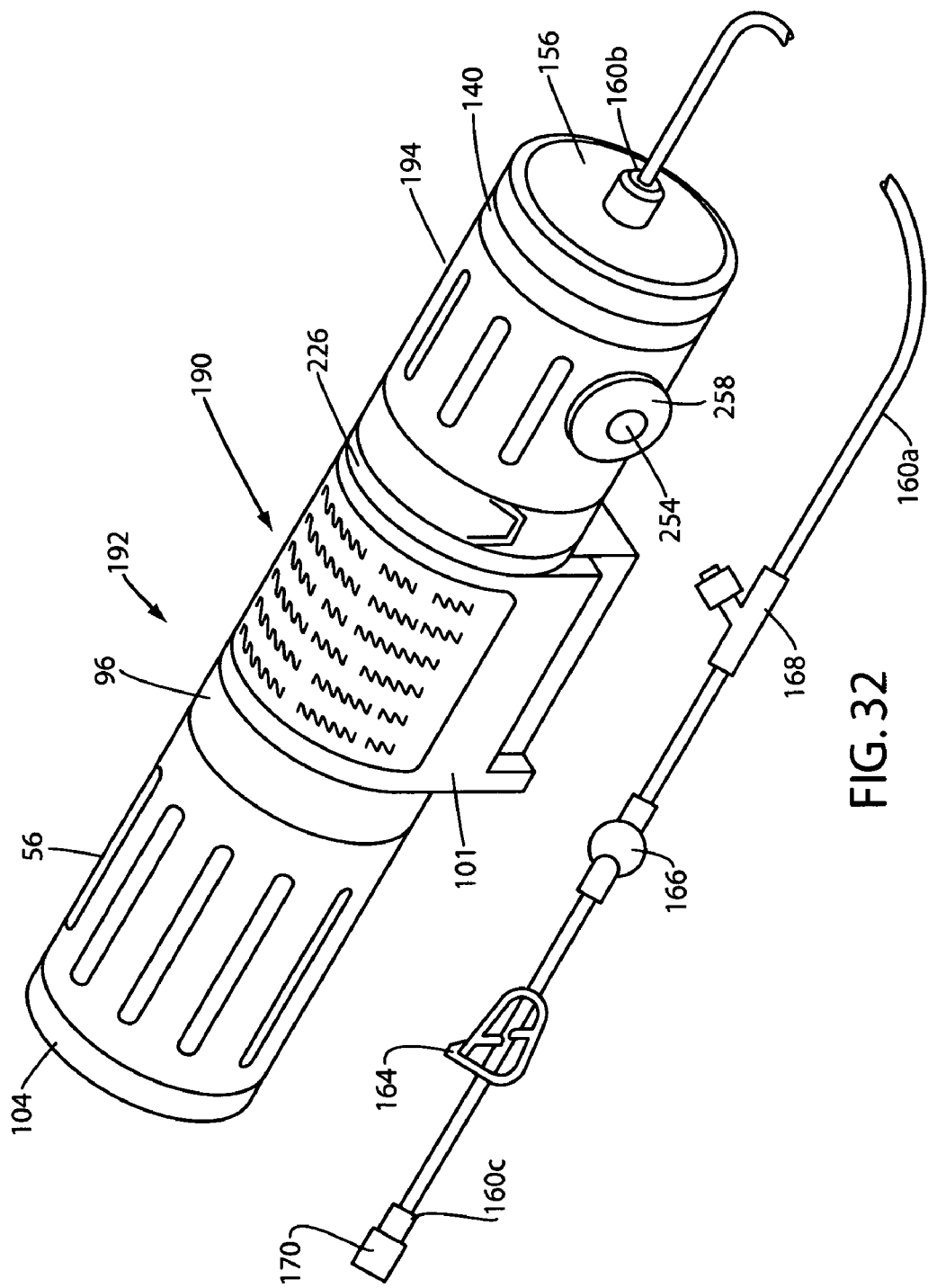
FIG. 32 is a generally perspective top view of an alternate form of the fluid dispensing device of the invention for dispensing medicaments to a patient.

Referring next to FIGS. 32 through 62 of the drawings, an alternate form of the fluid dispensing apparatus of the invention is there illustrated and generally designated in FIG. 32 by the numeral 190. This alternate form of the invention is similar in many respects that disclosed in FIGS. 1 through 32 and like numerals are used in FIGS. 32 through 62 to identify like components. One of the major differences between this latest embodiment of the invention and that earlier described herein resides in the provision of a collapsible container of a somewhat different configuration. Another difference resides in the provision of means for filling the reservoir of the collapsible container.

As in the earlier described embodiment, the dispensing apparatus of this alternate form of the invention comprises first and second operably associated assemblies 192 and 194. As best seen in FIG. 34 of the drawings, first assembly 192 comprises an internally threaded first housing 56 and an externally threaded shuttle housing 58 that is threadably connected to first housing 56 in the manner shown in FIGS. 33 and 34 of the drawings. First housing 56 and shuttle housing 58 are substantially identical in construction and operation to those previously described. As before, shuttle housing 58 has a wall 60 defining an axial passageway 62 and is provided with a pair of oppositely disposed openings 64 (see FIGS. 34 and 41).

Figure 35:
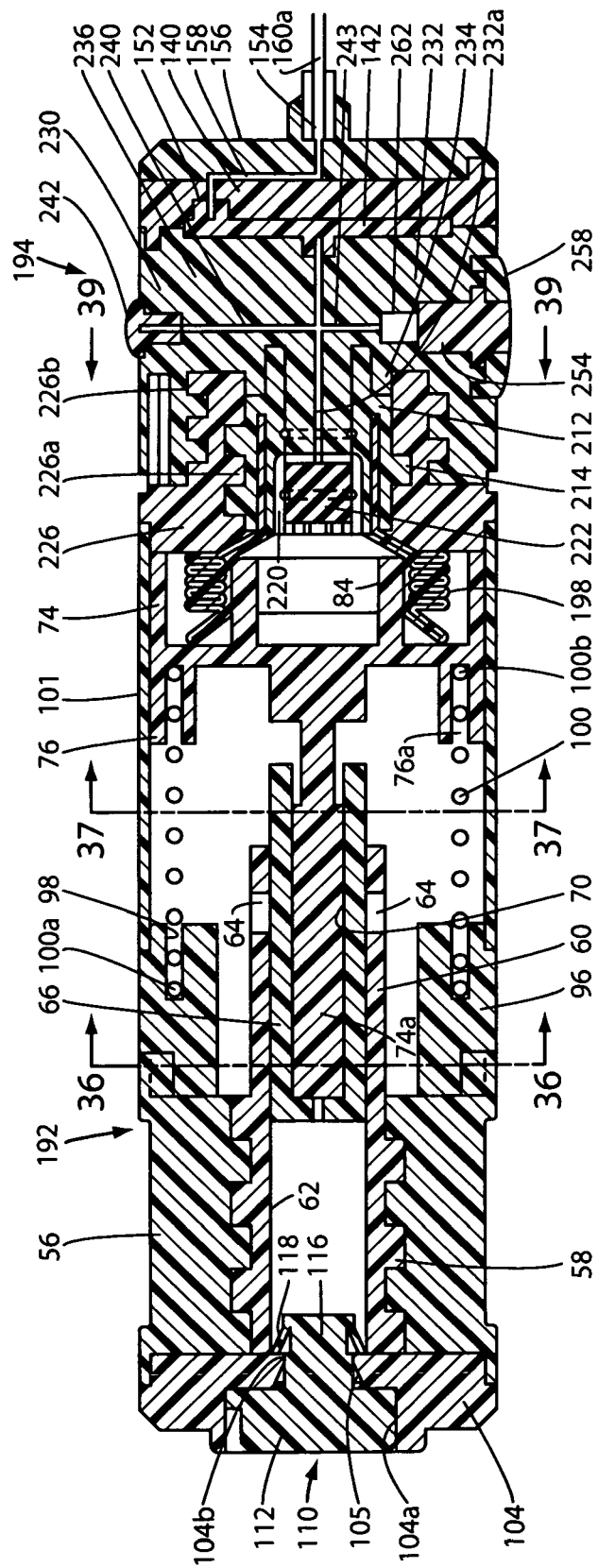
FIG. 35 is an enlarged, longitudinal cross-sectional view similar to FIG. 34, but showing the device as it appears after the medicaments have been dispensed to the patient.

Mounted within the axial passageway 62 of the shuttle housing for movement between a first retracted position shown in FIG. 34 and a second advanced position shown in FIG. 35 is a shuttle 66. Operably associated with shuttle 66 is a carriage assembly 72 that includes a carriage 74 having a shank portion 74a that is movable within axial passageway 70 between a first position shown in FIG. 4 and a second position shown in FIG. 5. Shuttle 66 and carriage assembly 72 are also substantially identical in construction and operation to those previously described.

As in the earlier described embodiment of the invention, the locking wings of the shank portion of the carriage 74, which comprise the locking means of this latest form of the invention, have end portions 80a that engage the forward walls 64a of the openings so as to prevent movement of the carriage 74 between its first position shown in FIG. 34 and its second position shown in FIG. 35.

Carried by carriage 74 is a reservoir assembly 196 that that is of a somewhat different construction and here comprises a collapsible container 198. As illustrated in FIG. 34 of the drawings, the bottom portion of the collapsible container 198 is received between the cylindrical head portion 76 of carriage 74 and a concentric, smaller diameter cylindrical portion 84.

As best seen in FIGS. 45 and 46 of the drawings, collapsible container 198 has an accordion-shaped side wall 200 that defines a collapsible reservoir 202 that has an outlet 204 and contains the medicinal fluid to be delivered to the patient. The accordion-shaped side wall 200 comprises a multiplicity of adjacent generally "V" shaped interconnected folds 200a. Collapsible container 198 has a neck portion 206 that is integrally formed with side wall 200. As in the earlier described embodiment, collapsible container 198 also uniquely includes an end wall 208 having an inwardly extending ullage defining protuberance 208a. As before, it is important that as much as possible of the beneficial agents contained within the collapsible container 198 be dispensed from a container to avoid improper dosage, waste and undue expense. Accordingly, ullage defining protuberance 208a functions to fill the interior space of the collapsible container when it is collapsed in the manner shown in FIG. 35 of the drawings.

Reservoir assembly 196 also includes an externally threaded flow control housing 212 that is connected to the neck portion 206 of the collapsible container 198 in the manner illustrated in FIG. 45 of the drawings. More particularly, housing 212 includes an outer, externally threaded portion 214 and a reduced diameter portion 216 that cooperate to define a generally cylindrically shaped passageway 218 that closely receives neck portion 206 of the collapsible container. Reduced diameter portion 216 of the flow control housing includes an inner wall portion 216a that is provided with a plurality of circumferentially spaced bypass flow channels 220, the purpose of which will presently be described. Also forming a part of container assembly 196 is a seal plug 222 that is slidably received within inner wall portion 216b of the flow control housing (FIG. 45) and, in a manner presently to be described, is movable between a first flow blocking position illustrated in FIGS. 34 and 45 of the drawings and a second flow permitting position illustrated in FIG. 35 of the drawings.

Interconnected with first housing 56 is a spring housing 96 that is substantially identical in construction and operation to that previously described. Spring housing 96 is provided with a circumferentially extending spring cavity 98 that receives the rear portion 100a of a coil spring 100 that comprises the stored energy means of this latest form of the invention for moving the carriage 74 of this latest embodiment of the invention from its first position to its second position. Carriage 74 is also substantially identical in construction and operation to that previously described and is released from its locked position by operation of the locking means of the invention which is also essentially identical in construction and operation to that previously described. More particularly, the generally cylindrical head portion 76 of the carriage 74 includes a circumferentially extending spring cavity 76a that receives the forward portion 100b of a coil spring 100 so that the spring can act directly on the carriage.

Connected to spring housing 96 and forming a part of the first assembly 192 of this latest form of the invention is a reservoir housing 101. Reservoir housing 101 interconnects spring housing 96 with an internally-externally threaded reservoir securement member 226. The internally threaded portion 226a of the reservoir securement member threadably engages the outer, externally threaded portion 214 of housing 212 so as to securely hold the container assembly 196 in position within the device in the manner illustrated in FIG. 34 of the drawings.

Connected to first housing 56 is a base member 104 that is provided with a first bore 104a of a first diameter and a second bore 104b of a second, lesser diameter. As before, second bore 104b includes a circumferentially extending groove 105. Rotatably mounted within bores 104a and 104b for movement between a first retracted position shown in FIG. 4 and a second advanced position shown in FIG. 5 is a carriage release assembly 110. Carriage release assembly 110, which is also essentially identical in construction and operation to the previously described carriage release assembly, is operably associated with the locking means of the invention for acting on the locking means to release the carriage 74 from its locked position.

Considering now the second assembly 194 of the dispensing apparatus, which is operably associated with first assembly 192, this important second assembly here comprises a novel fluid flow control means for controlling the flow of medicinal fluid toward the patient. As in the earlier described fluid flow control means, this latest fluid flow control means comprises two cooperating assemblies, namely a rate control assembly 122 for controlling the rate of fluid flow toward the patient and an operating assembly 230 for controlling the fluid flow between the device reservoir and the rate control assembly.

The rate control assembly 122 of this latest embodiment is substantially identical in construction and operation to that previously described and is illustrated in detail in FIGS. 23 through 29. However, the operating assembly 230 is somewhat different in construction and operation to that previously described. More particularly, operating assembly 230 here includes an internally threaded operating member 232 that is threadably connected to the externally threaded portion 226b of the reservoir securement member 226.

Operating member 232 is provided with a longitudinally extending central fluid passageway 232a and includes a reduced diameter pusher segment 234 and an enlarged diameter body segment 236. In a manner presently to be described, pusher segment 234 engages and moves the seal plug 222 from the first fluid flow blocking position illustrated in FIGS. 34 and 45 of the drawings to the second fluid flow permitting position illustrated in FIG. 35 of the drawings. Connected to the fluid passageway 232a and communicating therewith is a vent passageway 240 that, in turn, communicates with a gas vent port 242 formed in the body segment 236. Also connected to the fluid passageway 232a and communicating therewith is a fill passageway 243 that, in turn, communicates with the fill means of the invention, the character of which will presently be described, that functions to enable the controlled filling of the reservoir defining portion of the collapsible container of this latest form of the invention.

Connected to operating assembly 230 in the manner illustrated in FIG. 34 of the drawings is the previously discussed rate control means of the invention for controlling the rate of fluid flow from reservoir 90 toward the patient (see FIGS. 23 through 29). As before, the important rate control means of the invention here comprises a rate control housing 140 that houses the rate control assembly 142 of the invention (FIG. 26) that includes a rate control plate 144 having a serpentine micro-channel 146 that is provided with an inlet 148 and an outlet 150. Outlet 150 communicates with an outlet port 152 formed in rate control housing 140 and with an outlet passageway 154 that, in turn, communicates with a longitudinally extending outlet passageway 158 formed in closure member 156. As previously mentioned, outlet passageway 158 communicates with the administration line 160a of the administration set 160 of the apparatus which is substantially identical in construction and operation to that previously described.

Figure 33:
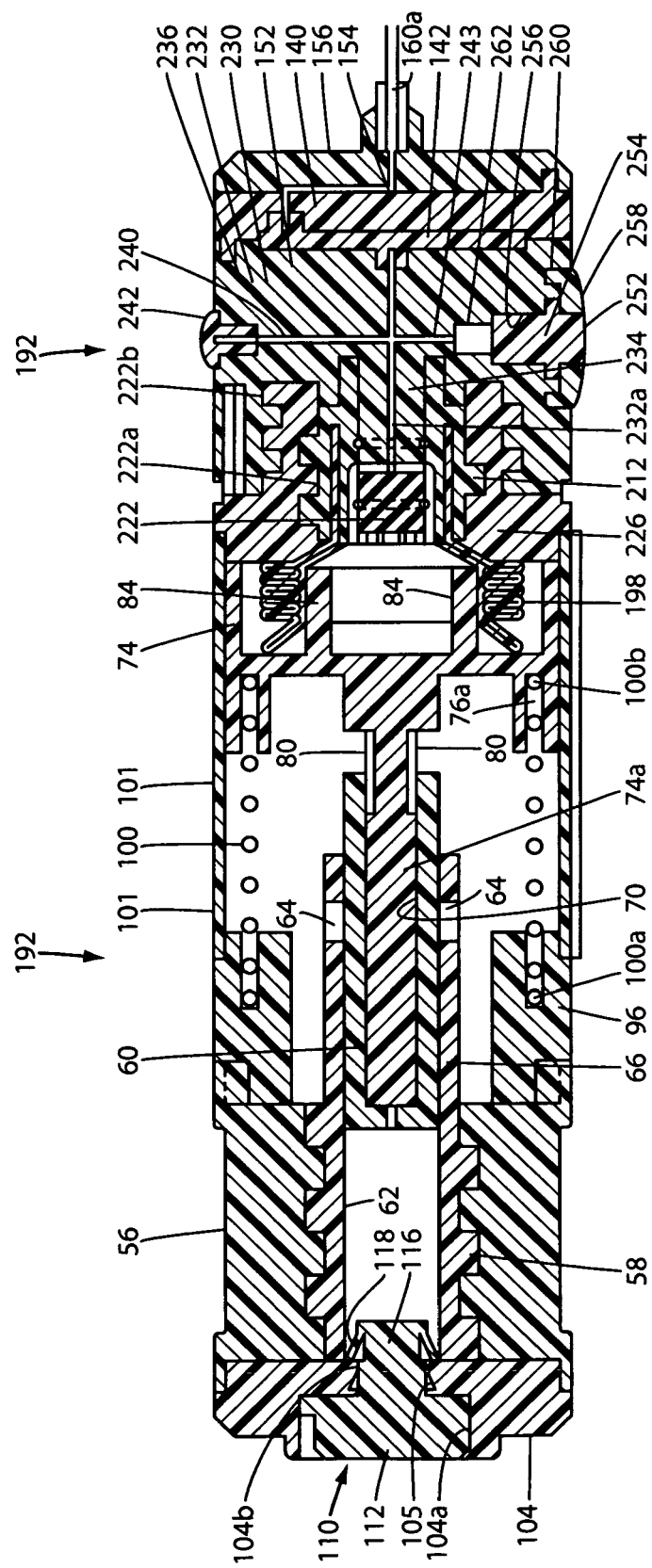
FIG. 33 is a longitudinal cross-sectional view of the dispensing device shown in FIG. 32 as it appears in the manufactured configuration.
Figure 33A:
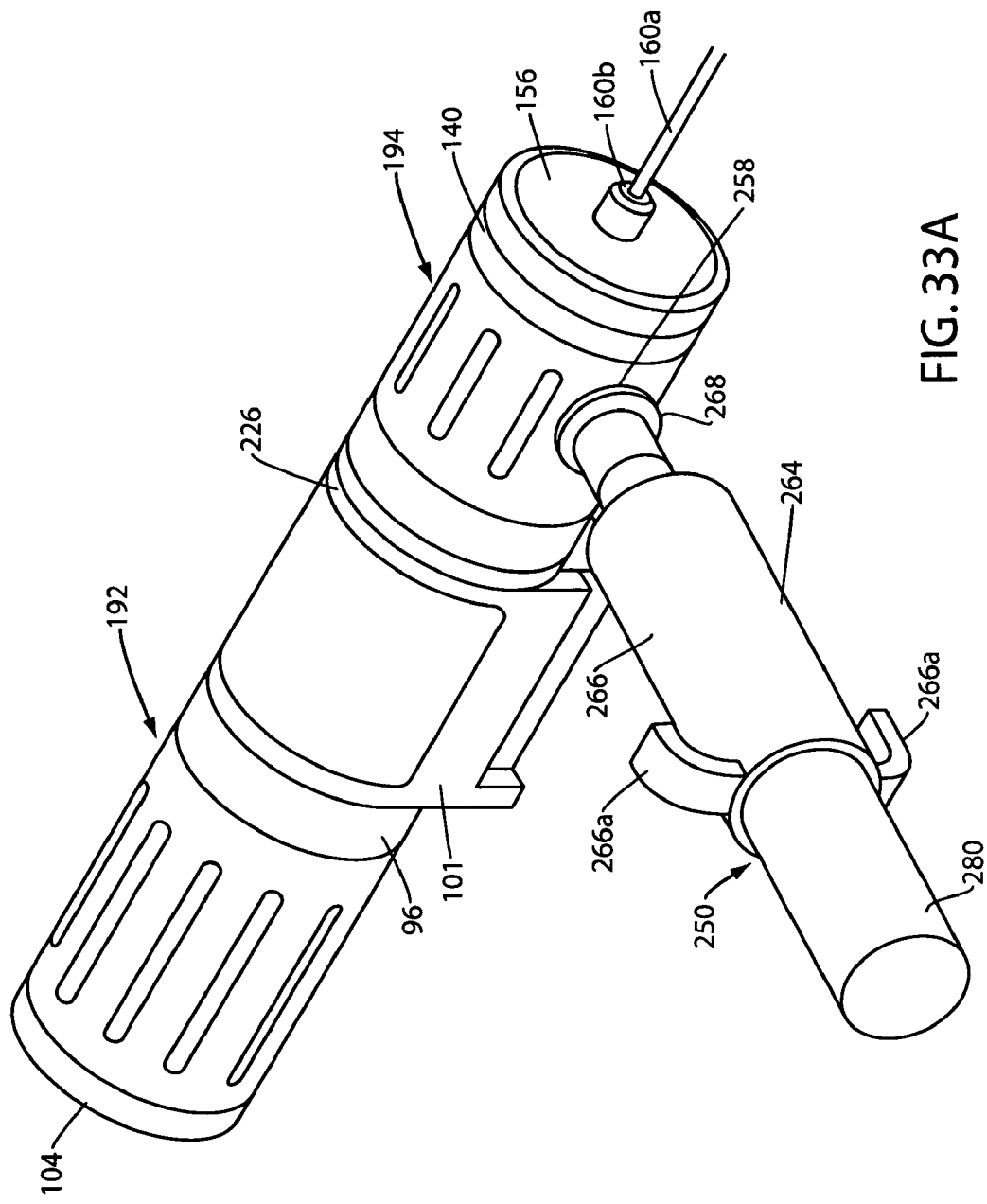
FIG. 33A is a generally perspective top view of the alternate form of the fluid dispensing device showing the reservoir fill assembly of the invention interconnected with the dispensing device.

In using the apparatus of this latest form of the invention, with the apparatus in the manufactured condition illustrated in FIG. 33 of the drawings, wherein the collapsible container 98 is empty, the first step in the operation of this latest form of the device is to use the fill means of the invention to fill the fluid reservoir with the beneficial agent to be delivered to the patient. This first step is accomplished by interconnecting the reservoir fill assembly 250 (see FIGS. 33A, 59 and 60) with the device fill port 252 (FIG. 34). Fill assembly 250 as well as fill port 252 comprise a part of the fill means of the invention.

As best seen in FIGS. 34 and 34A, the device fill port 252 here comprises a conventional slit septum 254 that is carried within a chamber 256 provided in operating member 232. Septum 254 is secured within chamber 256 by means of a closure member 258 that includes a pair of circumferentially spaced apart locking ears 260, the purpose of which will presently be described. As indicated in FIG. 34, chamber 256 is in communication with a reduced diameter chamber 262 that, in turn, is in communication with the earlier identified passageway 243.

Forming a part of the fill assembly 250 is the syringe assembly of the invention 264, which is interconnectable with the device fill port. Syringe assembly 264, the construction of which is illustrated in FIG. 59, comprises a hollow housing 266 that is provided proximate its forward end with a connector hub 268 that houses a blunt end cannula 270. Connector hub 268 is provided with a pair of circumferentially spaced connector openings 272 that lockably receive the previously identified, circumferentially spaced apart locking ears 260 formed on closure member 258 so that the syringe assembly can be securely interconnected with the device fill port. Connector openings 272 also lockably receive connector ears 276 that are provided on a closure cap 278 that functions to close connector hub 268 and protect the slit septum when the syringe is not in use. Disposed within housing 266 is a pusher member 279, the purpose of which will presently be described. During the reservoir filling step, the elastomeric plunger 282 is telescopically movable within the fluid container from the first advanced position shown in FIG. 59 to a second position wherein it resides proximate end wall 280*a*.

In accomplishing the reservoir fill step, the syringe assembly is interconnected with the dispensing device by mating the connector hub 268 with the closure member 258 and in so doing causing the blunt end cannula 270 to penetrate the slit septum 254. As the syringe assembly is pushed inwardly relative to the closure member, a concomitant rotation of the syringe assembly will cause the locking ears 260 provided on the locking member to lock the syringe assembly securely in place.

With the syringe assembly interconnected with the dispensing device the finger engaging ears 266*a* are gripped by the fingers of the caregiver and an inward pressure is exerted on the fluid container 280. This inward pressure will cause the pusher member 279 to move the elastomeric plunger 282 inwardly of the fluid reservoir 280*b*. Inward movement of plunger will, in turn, cause the fluid "F" contained within the reservoir 280*b* to flow into flow passageway 270*a* of the blunt end cannula, into passageways 236, past seal plug 222 via the plurality of circumferentially spaced bypass flow channels 220, and finally into the device reservoir 202.

As the reservoir 202 of the collapsible container 196 fills, fluid pressure will urge the seal plug from the position shown in FIG. 33 to the blocking position shown in FIG. 34. Fluid flowing into the empty container shown in FIG. 33 will cause the container to fill and expand into the filled configuration shown in FIG. 30. As the container fills and expands, the carriage assembly 72 is moved rearwardly from the advanced position shown in FIG. 33 to the position shown in FIG. 34. As the carriage assembly moves rearwardly, it will compress spring 100 and will also move the shuttle 66 rearwardly from the advanced position shown in FIG. 33 to the rearward position shown in FIG. 34. As the shuttle moves rearwardly, the pair of outwardly extending, yieldably deformable locking wings 80 formed on the shank portion of the carriage will extend through the openings 64 provided in shuttle housing 58 and into the carriage lock position shown in FIG. 34 so as to prevent movement of the carriage 74 between its first position shown in FIG. 34 and its second position shown in FIG. 35.

With the fluid reservoir filled in the manner described in the preceding paragraphs and with the apparatus in configuration illustrated in FIG. 34 of the drawings, the fluid delivery step can be commenced. The first operation in the fluid delivery step involves the rotation of the internally threaded operating member 232 relative to the externally threaded portion 226*b* of the reservoir securement member 226 in the manner illustrated in FIG. 61 of the drawings. This will cause the reduced diameter pusher segment 234 to engage and move the seal plug 222 from the first fluid flow blocking position illustrated in FIG. 34 of the drawings to the second fluid flow, permitting the position illustrated in FIG. 35 of the drawings, thereby opening communication between the fluid passageway and the fluid reservoir 202 of the collapsible container.

Figure 38:
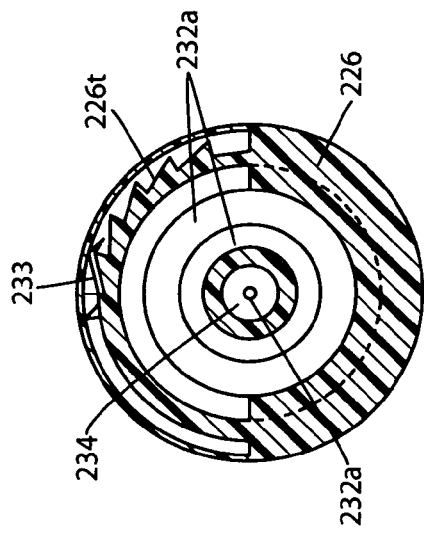
FIG. 38 is a cross-sectional view taken along lines 38-38 of FIG. 34.
Figure 37:
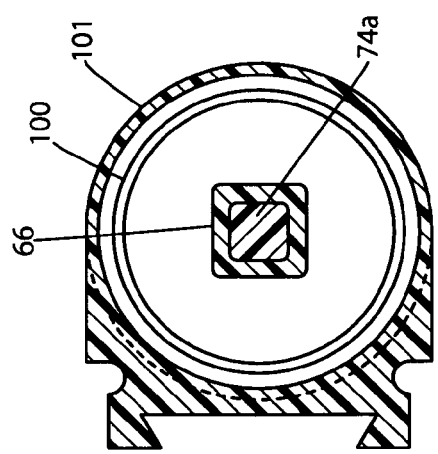
FIG. 37 is a cross-sectional view taken along lines 37-37 of FIG. 35.

As illustrated in FIG. 38, a portion of the inner wall of the reservoir securement member 226 is provided with a plurality of tooth-like cavities 226*t*. As the operating member 232 is rotated, an inwardly extending tab 233 provided on the operating member rides over tooth-like cavities and permits rotation of the operating member 232 in one direction, but positively prevents its rotation in the opposite direction. With this construction, accidental reverse rotation of the operating member 232 is positively prevented.

With communication opened between the fluid passageway 236 and the fluid reservoir 202, the next step in the operation of the apparatus of this latest form of the invention involves the manipulation of the carriage release assembly 110 to release the carriage from its locked position. This is accomplished in the manner previously described in connection with the earlier embodiment of the invention. More particularly, as illustrated in FIG. 62 of the drawings, this operation is accomplished by first gripping the finger engaging head portion 114 of the release member 112 and rotating it to the position shown in FIG. 3 of the drawings wherein it can be pushed inwardly of bores 104*a* and 104*b*. As the release member is pushed inwardly, the shank portion 116 thereof engages the shuttle 66 and urges it forwardly into the position shown in FIG. 35 of the drawings. As the shuttle 66 moves forwardly, the yieldably deformable locking tabs 118 will be urged inwardly into the flattened position shown in FIG. 35, thereby releasing the carriage 74 from its locked position.

Figure 36:
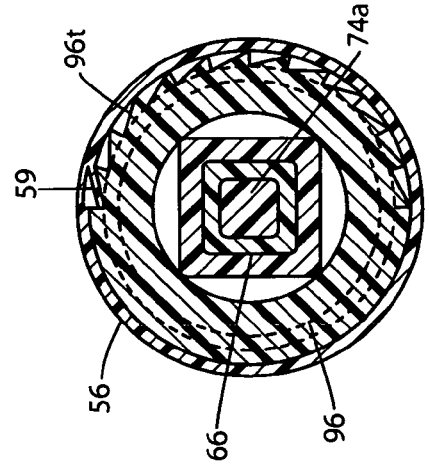
FIG. 36 is a cross-sectional view taken along lines 36-36 of FIG. 35.
Figure 39:
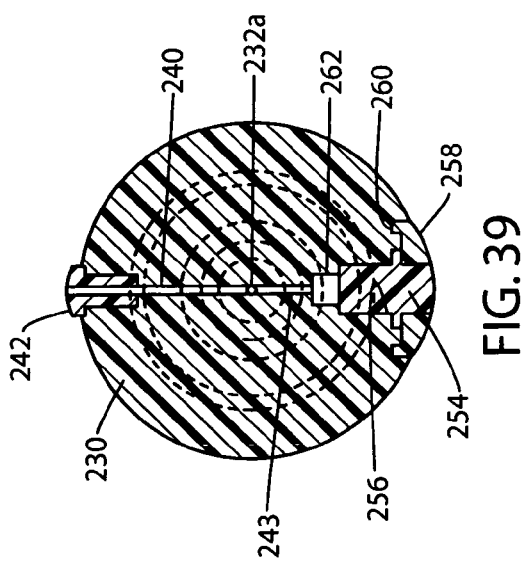
FIG. 39 is a cross-sectional view taken along lines 39-39 of FIG. 35.
Figure 49:
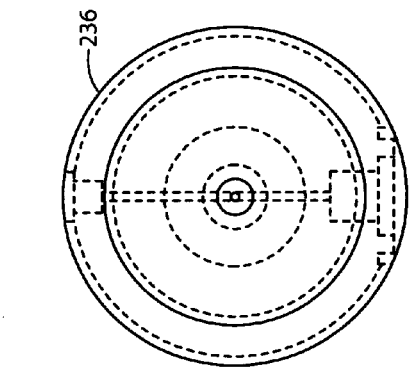
FIG. 49 is a view taken along lines 49-49 of FIG. 48.
Figure 52:
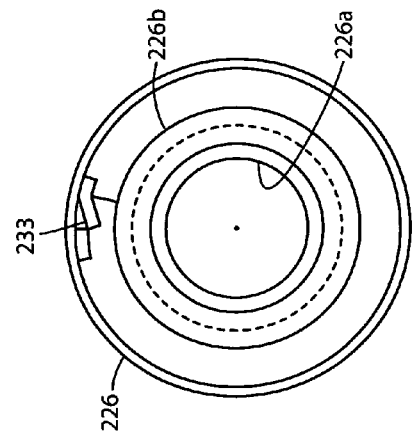
FIG. 52 is a view taken along lines 52-52 of FIG. 50.
Figure 48:
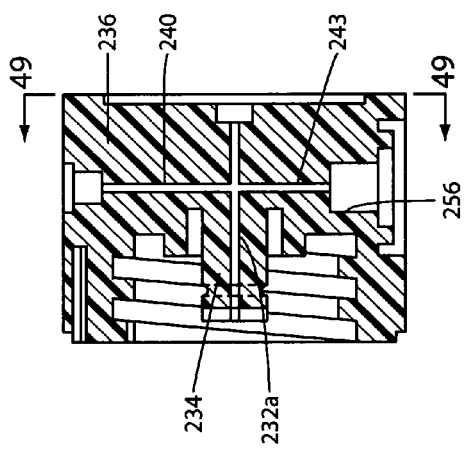
FIG. 48 is a cross-sectional view taken along lines 48-48 of FIG. 47.
Figure 50:
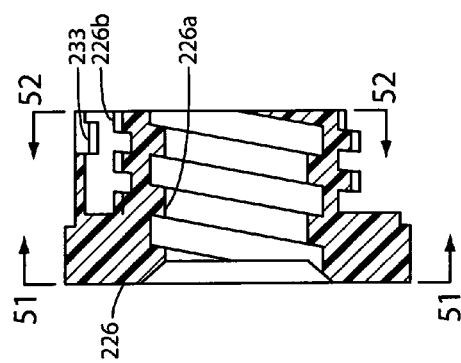
FIG. 50 is a cross-sectional view of the reservoir mounting housing of this latest form of the invention.
Figure 47:
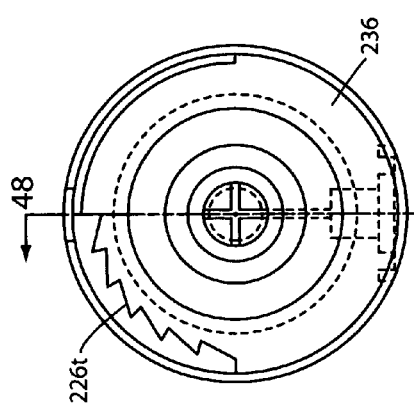
FIG. 47 is a rear view of the reservoir of the plunger housing component of this latest form of the invention.
Figure 51:
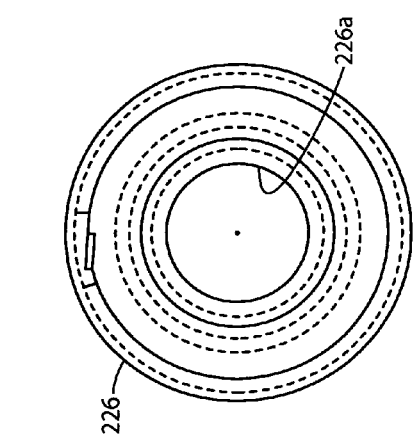
FIG. 51 is a view taken along lines 51-51 of FIG. 50.
Figure 55:
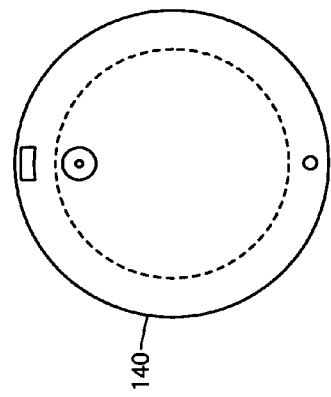
FIG. 55 is a view taken along lines 55-55 of FIG. 54.
Figure 58:
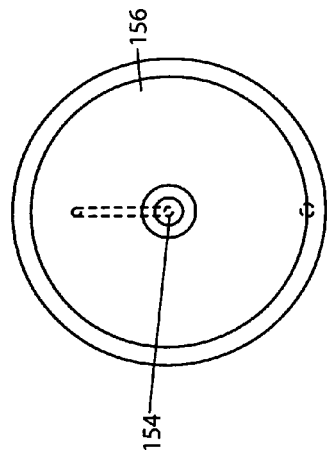
FIG. 58 is a view taken along lines 58-58 of FIG. 57.
Figure 54:
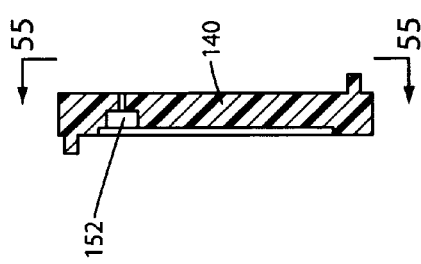
FIG. 54 is a cross-sectional view taken along lines 54-54 of FIG. 53.
Figure 57:
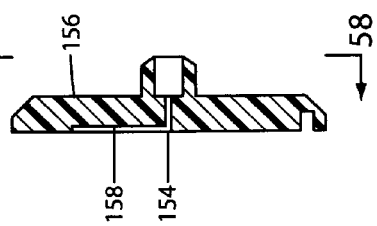
FIG. 57 is a cross-sectional view taken along lines 57-57 of FIG. 56.
Figure 53:
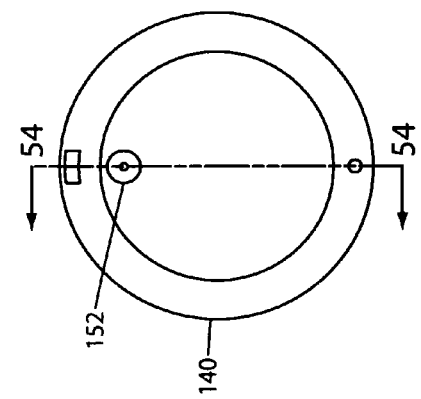
FIG. 53 is a rear view of the rate control housing of this latest form of the dispensing device.
Figure 56:
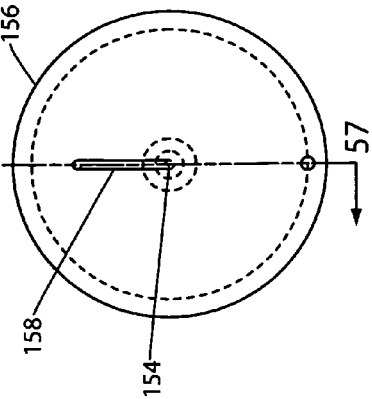
FIG. 56 is a rear view of the front closure component of this latest form of the dispensing device.
Figure 61:
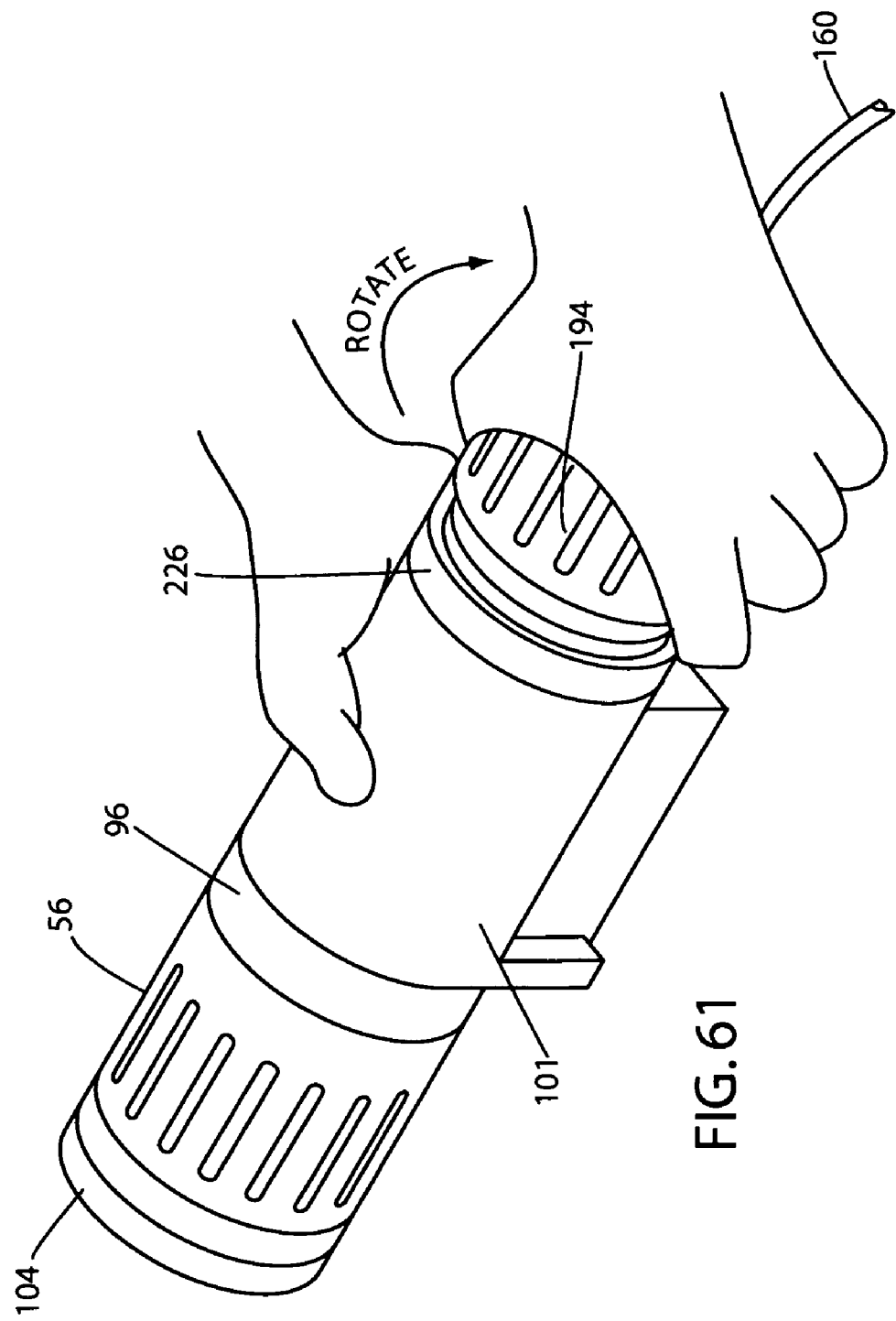
FIG. 61 is a generally perspective, diagrammatic view illustrating the first step in the operation of the apparatus of this latest form of the invention.

As before and as illustrated in FIG. 36 of the drawings, a portion of the circumference of spring housing 96 is provided with a plurality of tooth-like protuberances 96*t*. As housing 56 is rotated, a resiliently deformable inwardly extending tab 59 provided on housing 56 rides over the tooth-like protuberances and permits rotation of the housing in one direction, but positively prevents its rotation in the opposite direction. With this construction, accidental reverse rotation of the housing is positively prevented.

Upon release of the carriage assembly as a result of the inward movement of the release member 112, the stored energy means, or spring 100, will move the carriage from its locked position shown in FIG. 34 into the advanced position shown in FIG. 35 and in so doing will collapse the container 198. As the container collapses, the fluid contained there within will flow past the seal plug 222 via the circumferentially spaced bypass flow channels 220 and into the longitudinally extending central fluid passageway 236 and then into the inlet 148 of the serpentine micro-channel 146. The fluid will flow through the micro-channel 148 at a controlled rate depending upon the depth, width and length of the micro-channel and outwardly of the micro-channel outlet 150. From outlet 150 medicinal fluid will flow from the outlet port 152 formed in rate control housing 140 and into the outlet passageway 154 formed in a forward closure member 156. From outlet passageway 154, the fluid will flow into longitudinally extending outlet passageway 158 and onward to the patient via the administration set of the invention.

As before, this latest form of the apparatus also includes a belt clip 174 of the construction previously described that can be affixed to the reservoir housing 101 of the device so that, if desired, the device can be carried on the belt of the user.

Having now described the invention in detail in accordance with the requirements of the patent statutes, those skilled in this art will have no difficulty in making changes and modifications in the individual parts of their relative assembly in order to meet specific requirements or conditions. Such changes and modifications may be made without departing from the scope and spirit of the invention, as set forth in the following claims.

The invention claimed is:

1. A fluid dispensing apparatus for dispensing medicaments to a patient comprising:
   (a) a first assembly comprising:
      (i) a threaded first housing;
      (ii) a threaded shuttle housing threadably connected to said first housing, said shuttle housing having a wall defining an axial passageway;
      (iii) a shuttle mounted within said axial passageway of said shuttle housing for movement between a first retracted position and a second advanced position, said shuttle having a wall defining an axial passageway;
      (iv) a carriage assembly operably associated with said shuttle, said carriage being movable between a first position and a second position;
      (v) a spring operably associated with said carriage for moving said carriage between said first position and said second position;
      (vi) a reservoir assembly carried by said carriage assembly; and
   (b) a second assembly operably associated with said first assembly, said second assembly comprising a fluid flow control means comprising:
      (i) an operating means for controlling the flow of medicinal fluid toward the patient; and
      (ii) rate control means for controlling the rate of fluid flow from said collapsible container toward the patient.

2. The fluid dispensing apparatus as defined in claim 1 in which said reservoir assembly comprises a unitary pre-filled collapsible container having a continuous wall, said continuous wall including an end wall having an inwardly extending protuberance.

3. The fluid dispensing apparatus as defined in claim 1 in which said reservoir assembly comprises a collapsible container having a continuous accordion-shaped side wall that includes a multiplicity of adjacent generally "V" shaped interconnected folds and an open neck portion that is integrally formed with said side wall.

4. The fluid dispensing apparatus as defined in claim 1 in which said rate control means comprises a rate control plate having a micro-channel and a rate control cover connected to said rate control plate.

5. The fluid dispensing apparatus as defined in claim 1 further comprising an administration set, including an administration line interconnected with said outlet of said reservoir.

6. The fluid dispensing apparatus as defined in claim 1 in which said reservoir assembly comprises a collapsible container having a continuous accordion-shaped side wall and a open neck portion, in which said operating means comprises an operating member having a device fill port and in which said fluid dispensing apparatus further includes a reservoir fill assembly inter-connectable with said device fill port.

7. The fluid dispensing apparatus as defined in claim 1 in which said reservoir assembly comprises a collapsible container having a continuous accordion-shaped side wall and a open neck portion connected to said side wall and in which said operating means comprises an operating member having an enlarged diameter body segment, a reduced diameter pusher segment and a longitudinally extending central fluid passageway.

8. The fluid dispensing apparatus as defined in claim 1 in which said wall of said threaded shuttle housing has a pair of oppositely disposed openings and in which said carriage has a pair of outwardly extending, yieldably deformable locking wings, a portion of said locking wings extending through said openings provided in said wall of said shuttle housing to prevent movement of said carriage between said first position and said second position.

9. The fluid dispensing apparatus as defined in claim 1 in which said reservoir assembly comprises:
   (a) a unitary collapsible container having a pre-filled reservoir and a neck portion having a closure wall;
   (b) a pierceable membrane superimposed over said closure wall; and
   (c) a closure cap affixed to said neck portion.

10. The fluid dispensing apparatus as defined in claim 9 in which said operating means comprises an operating member, including a piercing member for piercing said closure wall and said pierceable membrane.

11. A fluid dispensing apparatus for dispensing medicaments to a patient comprising:
   (a) a first assembly comprising:
      (i) an internally threaded first housing;
      (ii) an externally threaded shuttle housing threadably connected to said internally threaded first housing, said shuttle housing having a wall defining an axial passageway, said wall having a pair of oppositely disposed openings;
      (iii) a shuttle mounted within said axial passageway of said shuttle housing for movement between a first retracted position and a second advanced position, said shuttle having an inner wall defining an axial passageway;
      (iv) a carriage assembly operably associated with said shuttle, said carriage assembly including a carriage having a shank portion movable within said axial passageway of said shuttle between a first position and a second position, said shank portion having a pair of outwardly extending, yieldably deformable locking wings, a portion of said locking wings extending through said openings provided in said wall of said shuttle housing;
      (v) a reservoir assembly carried by said carriage assembly;
      (vi) a spring housing interconnected with said first housing; and
      (vii) a spring carried by said spring housing, said spring being operably associated with said carriage for moving said carriage between said first position and said second position; and
   (b) a second assembly operably associated with said first assembly, said second assembly comprising a fluid flow control means comprising:
      (i) an operating means for controlling the flow of medicinal fluid toward the patient; and (ii) rate control means for controlling the rate of fluid flow from said collapsible container toward the patient.

12. The fluid dispensing apparatus as defined in claim 11 in which said first assembly further comprises:
(a) a base member connected to said first housing, said base member having a central bore and a circumferentially extending groove; and
(b) a carriage release assembly mounted within said central bore of said base member, said carriage release assembly comprising a finger engaging head portion and a shank portion disposed in engagement with said shuttle, said shank portion having outwardly extending, yieldably deformable locking tabs receivable within said circumferentially extending groove of said base.

13. The fluid dispensing apparatus as defined in claim 11 in which said reservoir assembly comprises a unitary pre-filled collapsible container having a continuous wall, said continuous wall including an end wall having an inwardly extending protuberance.

14. The fluid dispensing apparatus as defined in claim 11 in which said rate control means comprises a rate control plate having a micro-channel and a rate control cover connected to said rate control plate.

15. The fluid dispensing apparatus as defined in claim 11 in which said reservoir assembly comprises a collapsible container having a continuous accordion-shaped side wall and a open neck portion, in which said operating means comprises an operating member having a device fill port and in which said fluid dispensing apparatus further includes a reservoir fill assembly inter-connectable with said device fill port.

16. The fluid dispensing apparatus as defined in claim 15 in which said first assembly further comprises:
(a) a threaded reservoir securement member;
(b) a threaded flow control housing threadably connected to said threaded reservoir securement member, said flow control housing having a passageway for receiving said open neck portion of said container and an inner wall portion provided with a plurality of circumferentially spaced bypass flow channels; and
(c) a seal plug slidably receivable within said inner wall portion of said flow control housing, said seal plug being movable within said inner wall portion between a first flow blocking position and a second flow permitting position.

17. A fluid dispensing apparatus for dispensing medicaments to a patient comprising:
(a) a first assembly comprising:
(i) an internally threaded first housing;
(ii) an externally threaded shuttle housing threadably connected to said internally threaded first housing, said shuttle housing having a wall defining an axial passageway, said wall having a pair of oppositely disposed openings;
(iii) a shuttle mounted within said axial passageway of said shuttle housing for movement between a first retracted position and a second advanced position, said shuttle having a wall defining an axial passageway;
(iv) a carriage assembly operably associated with said shuttle, said carriage assembly including a carriage having a shank portion movable within said axial passageway of said shuttle between a first position and a second position, said shank portion of said carriage having a pair of outwardly extending, yieldably deformable locking wings, a portion of said locking wings extending through said openings provided in said wall of said shuttle housing;
(v) a reservoir assembly carried by said carriage assembly, said reservoir assembly comprising a collapsible container having a side wall, a bottom wall and a neck formed of a single material, said bottom wall having an inwardly extending protuberance, said collapsible container having a reservoir containing medicinal fluid, said collapsible reservoir having an outlet;
(vi) a spring housing interconnected with said first housing, said spring housing having a circumferentially extending spring cavity;
(vii) a spring carried within said circumferentially extending spring cavity of said spring housing, said spring being operably associated with said carriage for moving said carriage between said first position and said second position;
(viii) a base member connected to said first housing, said base member having a central bore and a circumferentially extending groove; and
(ix) a carriage release assembly mounted within said central bore of said base member, said carriage release assembly comprising a finger engaging head portion and a shank portion disposed in engagement with said shuttle, said shank portion of said carriage release assembly having outwardly extending, yieldably deformable locking tabs receivable within said circumferentially extending groove of said base; and
(b) a second assembly operably associated with said first assembly, said second assembly comprising a fluid flow control means comprising:
(i) an operating means for controlling the flow of medicinal fluid toward the patient; and
(ii) rate control means for controlling the rate of fluid flow from said collapsible container toward the patient, said rate control means comprising a rate control plate having a micro-channel and a rate control cover connected to said rate control plate.

18. The fluid dispensing apparatus as defined in claim 17 in which said first assembly further comprises:
(a) a threaded reservoir securement member;
(b) a threaded flow control housing threadably connected to said threaded reservoir securement member, said flow control housing having a passageway for receiving said neck of said container and an inner wall portion provided with a plurality of circumferentially spaced bypass flow channels; and
(c) a seal plug slidably receivable within said inner wall portion of said flow control housing, said seal plug being movable within said inner wall portion of said control housing.

19. The fluid dispensing apparatus as defined in claim 17 in which said operating means comprises an operating member having a device fill port and in which said fluid dispensing apparatus further includes a reservoir fill assembly inter-connectable with said device fill port.

20. The fluid dispensing apparatus as defined in claim 17 in which said reservoir assembly comprises a unitary collapsible container having a pre-filled reservoir and a neck portion having a closure wall; a pierceable membrane superimposed over said closure wall; and in which said operating means comprises an operating member, including a piercing member for piercing said closure wall and said pierceable membrane.

* * * * *